(12) United States Patent
Idell

(10) Patent No.: US 7,332,469 B2
(45) Date of Patent: Feb. 19, 2008

(54) INTRAPLEURAL SINGLE-CHAIN UROKINASE ALONE OR COMPLEXED TO ITS SOLUBLE RECEPTOR PROTECTS AGAINST PLEURAL ADHESIONS

(75) Inventor: Steven Idell, Tyler, TX (US)

(73) Assignee: Board of Regents The University of Texas System, Austin, TX (US)

( * ) Notice: Subject to any disclaimer, the term of this patent is extended or adjusted under 35 U.S.C. 154(b) by 562 days.

(21) Appl. No.: 10/407,821

(22) Filed: Apr. 4, 2003

(65) Prior Publication Data

US 2003/0219386 A1 Nov. 27, 2003

Related U.S. Application Data

(60) Provisional application No. 60/414,202, filed on Sep. 27, 2002, provisional application No. 60/370,466, filed on Apr. 5, 2002.

(51) Int. Cl.
*C07K 14/00* (2006.01)
(52) U.S. Cl. .......................................... 514/2; 530/350
(58) Field of Classification Search ............. 514/2; 530/350
See application file for complete search history.

(56) References Cited

U.S. PATENT DOCUMENTS

| | | | | |
|---|---|---|---|---|
| 4,554,101 | A | 11/1985 | Hopp | 260/112.5 |
| 4,968,494 | A | 11/1990 | Claremon et al. | 424/94.64 |
| 5,399,363 | A | 3/1995 | Liversidge et al. | 424/490 |
| 5,466,468 | A | 11/1995 | Schneider et al. | 424/450 |
| 5,468,505 | A | 11/1995 | Hubbell et al. | 424/484 |
| 5,548,158 | A | 8/1996 | Bulucea et al. | 257/592 |
| 5,582,862 | A | 12/1996 | Reed et al. | 424/145.1 |
| 5,641,515 | A | 6/1997 | Ramtoola | 424/189 |
| 5,846,225 | A | 12/1998 | Rosengart et al. | 604/115 |
| 5,846,233 | A | 12/1998 | Lilley et al. | 604/414 |
| 6,280,730 | B1 | 8/2001 | Reed et al. | 424/141.1 |
| 6,833,357 | B2 * | 12/2004 | Cines et al. | 514/12 |
| 6,911,316 | B1 * | 6/2005 | Higazi | 435/13 |

FOREIGN PATENT DOCUMENTS

| JP | 9-104637 | 4/1997 |
|---|---|---|
| WO | WO 01/21761 | 3/2001 |

OTHER PUBLICATIONS

Bouros et al. Intrapleural Urokinase versus Normal Saline in the Treatment of Complicated Parapneumonic Effusions and Empyema. (1999) Am. J. Respir. Care Med. vol. 159, pp. 37-42.*
Munster et al. Jet and ultrasonic nebulization of single chain urokinase plasminogen activator (scu-PA) (2000 Winter) vol. 13, No. 4, pp. 325-333.*
Antony et al., "Pleural mesothelial cell expression of C-C (monocyte chemtactic peptide) and C-X-C (interleukin 8) chemokines," *Am. J. Respir. Cell Mol. Biol.*, 12:581-588. 1995.
Appella et al., "The receptor-binding sequence of urokinase," *J. Biol. Chem.*, 262(10):4437-4440, 1987.
Bajpai and Baker, "Cryptic urokinase binding sites on human foreskin fibroblasts," *Biochem. Biophys. Res. Commun.*, 133(2):475-482, 1985.
Bdeir et al., "Urokinase mediates fibrinolysis in the pulmonary microvasculature," *Blood*, 96:1820-1826, 2000.
Boyd et al, "Determination of the levels of urokinase and its receptor in human colon carcinoma cell lines," *Cancer Research*, 48:3112-3116, 1988.
Brixner, "Biotechnology products: an overview," *In: Biotechnology And Pharmacy*, Pezzuto et al., (eds.), Chapman and Hall (Eds.), NY, Chapter 15:381-401, 1993.
Brott and Bogousslavsky, "Treatment of acute Ischemic stroke," *N. Engl. J. Med.*, 343[10], 710-722. 2000.
Cameron and Davies, "Intra-pleural fibrinolytic therapy for parapneumonic effusions and empyema," *Cochrane Database Syst. Rev.*, 3:002312, pp. 1-26, 2000.
Coleman and Benach, "Use of the plaminogen activation system by microorganisms," *J. Lab. Clin. Med.*, 134:567-576, 1999.
Colice et al., "Medical and surgical treatment of parapneumonic effusions," *Chest*, 18:1158-1171, 2000.
Cubeilis et al., "Binding of single-chain prourokinase to the urokinase receptor of human U937 cells," *J. Biol. Chem.*, 261(34):15819-15822, 1986.
Davies et al., "The systemic fibrinolytic activity of intrapleural streptokinase," *Am. J. Respir. Crit. Care Med.*, 156:328-330, 1997.
de Souza et al., "Optimal management of complicated empyema," *Am. J. Surg.*, 180:507-511, 2000.
Dvorak, "Tumors: wounds that do not heal—similarities between tumor stroma generation and wound healing," *NE J. Med.*, 315:1650-1659, 1986.
Eaton et al., "Purification of human fibroblast urokinase proenzyme and analysis of its regulation by proteases and protease nexin," *J. Biol. Chem.*, 259(10):6241-6247, 1984.
Handley et al., "A role for urokinase-type plasminogen activator in human immunodeficiency virus type 1 infection of macrophages," *J. Virol.*, 70:4451-4456, 1996.

(Continued)

Primary Examiner—Karen Cochrane Carlson
(74) Attorney, Agent, or Firm—Browdy and Neimark P.L.L.C.

(57) ABSTRACT

The present invention relates to methods of preventing or decreasing the severity of scarring in a subject comprising: obtaining a pharmaceutical composition comprising a single chain urokinase plasminogen activator molecule (scuPA) or a scuPA mimetic; and administering the pharmaceutical composition to a subject; wherein scarring in the subject is either prevented or decreased relative to an amount of scarring that would be expected if the pharmaceutical composition were not administered to the subject. The invention also relates to methods of screening for compounds that prevent or decrease the severity of scarring in a subject.

6 Claims, 23 Drawing Sheets

OTHER PUBLICATIONS

Higazi et al., "Enhancement of the enzymatic activity of single-chain urokinase plasminogen activator by soluble urokinase receptor," *J. Biol. Chem.*, 270:17375-17380, 1995.

Higazi et al., "Lysis of plasma clots by urokinase-soluble urokinase receptor complexes," *Blood*, 92:2075-2083, 1998.

Higazi et al., "Single-chain urokinase-type plasminogen activator bound to its receptor is relatively resistant to plasminogen activator inhibitor type 1," *Blood*, 87:3545-3549, 1996.

Higazi et al., "Soluble human urokinase receptor is composed of two active units," *J. Biol. Chem.*, 272:5348-5353, 1997.

Idell et al., "Abnormalities of pathways of Fibrin turnover in the human pleural space," *Amer. Rev. Respir. Dis.*, 144:187-194, 1991.

Idell et al., "Single-chain urokinase alone or complexed to its receptor in tetracycline-induced pleuritis in rabbits," *Am. J. Respir. Crit. Care Med.*, 166:920-926, 2002.

Idell et al., "Tissue factor pathway inhibitor in tetracycline-induced pleuritis in rabbits," *Thromb. and Haemost.*, 79:649-655, 1998.

Idell, "Coagulation, fibrinolysis, and fibrin deposition in lung injury and repair," *In: Pulmonary Fibrosis,*. Thrall and Phan (Eds.), NY, Marcel Dekker, 80:Chapter 23, pp. 743-776. 1995.

Idell, "Extravascular coagulation and fibrin deposition in acute lung injury," *New Horizons*, 2:566-574, 1994.

Kasai et al., "Primary structure of single-chain pro-urokinase," *J. Biol. Chem.*, 260:12382-12389, 1985.

Kyte and Doolittle, "A simple method for displaying the hydropathic character of a protein," *J. Mol. Biol.*, 157(1):105-132, 1982.

Light et al., "Management of parapneumonic effusions," *Clin. Chest Med.*, 19:373-382, 1998.

Light, "Hemothorax," *In: Pleural Diseases*, 4th ed. Lippincott Williams and Wilkins, Philadelphia, Chapter 22, pp. 320-326, 2001.

Light, "Parapneumonic effusions and empyema," *In: Pleural Diseases*, 4th ed. Lippincott Williams and Wilkins, Philadelphia, Chapter 9, pp. 151-181, 2001.

Manchanda, "Interaction of single-chain urokinase and plasminogen activator inhibitor type 1," *J. Biol. Chem.*, 270:20032-20035, 1995.

Matsuo et al., "Thrombolytic effect of single-chain pro-urokinase in a rabbit jugular vein thrombosis model," *Thromb. Res.*, 42:187-194, 1986.

Mazar et al., "The urokinase plasminogen activator system in cancer: implications for tumor angiogenesis and metastasis," *Angiogenesis*, 3:15-32. 1999.

Miller et al., "Chemokine involvement in tetracycline-induced pleuritis," *Europ. Respir. J.*, 14:1387-1393, 1999.

Needham et al., "Binding of urokinase to specific receptor sites on human breast cancer membranes," *Br. J. Cancer*, 55:13-16, 1987.

Nielsen et al., "A 55,000-60,000 $M_r$ receptor protein for urokinase-type plasminogen activator," *J. Biol. Chem.*, 263:2358-2363, 1988.

Pannell and Gurewich, "Activation of plasminogen by single-chain urokinase or by two-chain urokinase—a demonstration that single-chain urokinase has a low catalytic activity (pro-urokinase)," *Blood*, 69:22-26, 1987.

Perkins et al., "Asbestos upregulates expression of the urokinase-type plasminogen activator receptor on mesothelial cells," *Am. J. Respir. Cell Mol. Biol.*, 21:637-646, 1999.

Ploug et al., "Glycosylation profile of a recombinant urokinase-type plasminogen activator receptor expressed in Chinese hamster ovary cells," *J. Biol. Chem.*, 273:13933-13943, 1998.

Plow et al., "The plasminogen system and cell surfaces: evidence for plasminogen and urokinase receptors on the same cell type," *J. Cell Biol.*, 103(6):2411-2420, 1986.

Sahn, "The pleura," *Am. Rev. Respir. Dis.*, 138:184-234, 1988.

Sahn, "Use of fibrinolytic agents in the management of complicated parapeneumonic effusions and empyemas," *Thorax*, 53(2):S65-S72, 1998.

Sahn, *In: Pleural Disease*, 2ed. American College of Physicians and Amer. Soc. Internal Med., Chapter 9, pp. 262-283, 1998.

Sambrook et al., *In: Molecular cloning*, Chapter 5, Protocol 2, pp. 5.14-5.17, Cold Spring Harbor Laboratory Press, Cold Spring Harbor, NY, 2001.

Shetty and Idell, "A urokinase receptor mRNA binding protein from rabbit lung fibroblasts and mesothelial cells," *Amer. J. Physiol.*, 274:L871-L882, 1998.

Shetty and Idell, "Urokinase induces expression of its own receptor in Bease2B lung epithelial cells," *J. Biol. Chem.*, 276:24549-24556, 2001.

Shetty et al., "Differential expression of the urokinase receptor in fibroblasts form normal and fibrotic human lungs," *Am. J. Respir. Cell Mol. Biol.*, 15:78-87, 1996.

Skriver et al., "Immunocytochemical localization of urokinase-type plasminogen activator in Lewis lung carcinoma," *J. Cell Biol.*, 99:752-757, 1984.

Stoppelli et al., "Differentiation-enhanced binding of the amino-terminal fragment of human urokinase plasminogen activator to a specific receptor on U937 monocytes," *Proc. Natl. Acad. Sci. USA*, 82:4939-4943, 1985.

Strange et al., "Effects of intrapleural heparin or urokinase on the extent of tetracycline-induced pleural disease," *Am. J. Respir. Crit Care Med.*, 151:508-515, 1995.

Tarui et al., "Urokinase-type plasminogen activator receptor (CD87) is a ligand for integrins and mediates cell-cell interaction," *J. Biol. Chem.*, 276(6):3983-3990. 2001.

Tillett and Sherry, "The effect in patients of streptococcal fibrinolysin (streptokinase) and streptococcal desoxyribonuclease on fibrinous, purulent, and sanguinous pleural exudations," *J. Clin. Invest.*, 28:173-190, 1949.

Vassalli et al., "A cellular binding site for the $M_r$ 55,000 form of the human plasminogen activator, urokinase," *J. Cell. Biol.*, 100:86-92, 1985.

Bouros et al., "Intrapleural urokinase in the treatment of complicated parapneumonic pleural effusions and empyema," *Eur Respir J*, 9:1656-1659, 1996.

Gram et al., "Inhalation/intravenous recombinanat tissue plasminogen activator and inhaled heparin in a patient with respiratory distress syndrome," *Fibrinolysis & Proteolysis*, 13:209-212, 1999.

Lahorra et al., "Safety of intracavitary urokinase with percutaneous abscess drainage," *AJR*, 160:171-174, 1993.

Pollak and Passik, "Intrapleural urokinase in the treatment of loculated pleural effusions," *Chest*, 105:868-873, 1994.

\* cited by examiner

APPENDIX A

Schematic Structures of Urokinase Plasminogen Activator (uPA)[1]

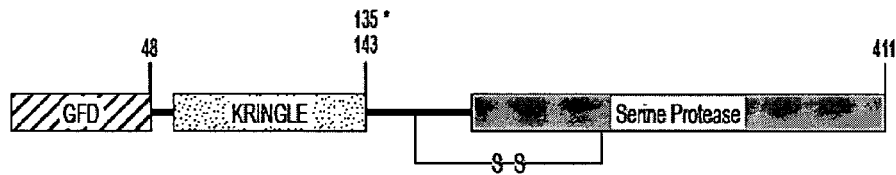

single chain uPA (scuPA) or
high molecular weight scuPA

FIG. 1

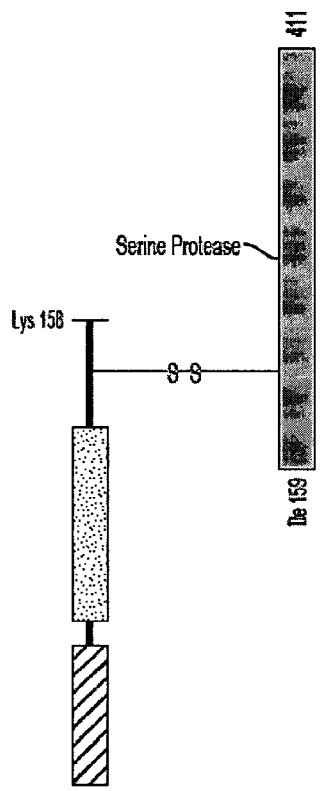

two-chain uPA (tcuPA)

1 * The C-terminal residue of the Kringle region is either 135 or 143 of the original scuPA sequence, depending on which protease was used to cleave the kringle region. Accordingly, the low molecular weight scuPA or tcuPA (Figs. 3 and 4) begin at position 136 or 144 of the original sequence.

APPENDIX A
(page 2)

Low molecular weight scuPA

Low molecular weight tcuPA
("Abbokinase")

INTRAPLEURAL SINGLE-CHAIN UROKINASE ALONE OR COMPLEXED TO ITS SOLUBLE RECEPTOR PROTECTS AGAINST PLEURAL ADHESIONS

This application claims the benefit of U.S. Provisional Application No. 60/370,466 filed Apr. 5, 2002, and U.S. Provisional Application No. 60/414,202 filed Sep. 27, 2002, the entire disclosures of which are incorporated herein by reference.

The government owns rights in the present invention pursuant to grant number NIH RO-1 HL45018 from The National Institutes of Health (NIH), National Heart, Lung and Blood Institute (NHLBI).

BACKGROUND OF THE INVENTION

1. Field of the Invention

The present invention relates generally to the fields of molecular biology and therapy for pleural diseases. More particularly, the present invention concerns single chain urokinase plasminogen activator (scuPA) in pleural disease.

2. Description of Related Art

The pathogenesis of pleural loculation recapitulates that of wound healing, with a progression of extravascular fibrin deposition and remodeling of transitional fibrin leads to fibrotic repair and scar formation (Dvorak, 1986). The injured pleural space is an inhibitor-rich environment, which limits expression of endogenous PA activity. Pleural fluid fibrinolytic activity is generally depressed in exudative pleural effusions and in this respect recapitulates the response observed in alveolar lining fluids in ARDS (Idell, 1994). For example, there is almost always no detectable fibrinolytic activity in pleural fluids from patients with parapneumonic effusions and empyema and procoagulant activity is concurrently augmented (Idell et al., 1991). These conditions favor the deposition and maintenance of intrapleural fibrin in the setting of high-grade local inflammation. While the pleural fluids contain both tPA and uPA, most of the immunoreactive PA is bound and irreversibly inhibited by PAI, mainly PAI-1 (Idell et al., 1991). Only small amounts of immunoreactive free uPA, but not tPA are detectable and uPA is present in amounts insufficient to overcome inhibition by PAI-1 and antiplasmins that further damp the expression of fibrinolytic activity in these fluids. Fibrinolytic activity is likewise undetectable in pleural effusions that form after TCN-induced pleuritis in rabbits attributable to the identical expression of PAI-1 and antiplasmins (Strange et al., 1995). These circumstances likely limit the fibrinolytic activity of the currently used fibrinolysins.

A phase of fibrinous adhesion formation initiates intrapleural loculation and fibrosis (Sahn, 1988; Light, 2001). Morphologic evidence from TCN-induced pleural injury in rabbits directly links transitional extravascular fibrin deposition to the pathogenesis of intrapleural loculation after acute pleural injury (Idell et al., 1998; Strange et al., 1995). Intrapleural loculation can occur early in the course of complicated parapneumonic effusions or frank empyemas and can adversely affect clinical outcome (Sahn, 1988; Light, 2001). It has long been appreciated that an initial fibrinopurulent phase occurs as part of the inflammatory response. During this phase, intrapleural fibrin forms and can bridge the visceral and parietal pleural surfaces (Sahn, 1988; Light, 2001; Sahn, 1998a). If the inflammatory process persists, the fibrinous exudate undergoes organization, with fibroblast invasion and collagen deposition (Light, 2001). Clinically, formation of a "pleural peel" and extensive intrapleural organization can encase the lung and impair its function. A similar process of intrapleural fibrin deposition and organization can occasionally occur in association with hemothoraceses, supporting the concept that intrapleural fibrin formation is integral to subsequent loculation and scarring in the pleural compartment (Light, 2001).

Intrapleural fibrin deposition can be targeted for therapeutic benefit. Tillett and Sherry originally used relatively crude preparations of streptokinase to degrade pleural loculations (Tillett and Sherry, 1949). This fibrinolytic strategy has been refined and remains a viable clinical option for treatment of loculated parapneumonic effusions (Sahm, 1988; Light, 2001; Sahn, 1998b; Light et al., 1998; Colice et al., 2000). However, the use of intrapleural fibrinolysins can be logistically difficult and expensive in that multiple treatments are often required and hospital stay is often extended, providing the rationale to investigate whether alternative agents could be effective and safe for intrapleural application.

Previous studies have found that administration of intrapleural heparin or the no-longer commercially available low molecular weight (LMW) uPA; Abbokinase (Abbott Laboratories, North Chicago, Ill.) could attenuate intrapleural adhesion formation induced by intrapleural administration of TCN in rabbits. Multiple doses of heparin or intrapleural LMW uPA; every 12 hr over 72 hr were required to achieve partial protection against formation of intrapleural adhesions in this study. However, the protection provided by LMW uPA was found to be incomplete.

There is ongoing debate about the place of currently available fibrinolytic interventions for intrapleural loculation. In a recent systemic review of all available randomized controlled trials, the pooled data showed that small benefits of fibrinolytic intervention could be anticipated in terms of reduction of hospital stay, time to defervescence, radiographic improvement and ultimate need for surgical intervention (Cameron, 2000). Based on this analysis, it was concluded that there was insufficient rate evidence to support the routine use of fibrinolysins in this context. In another recent retrospective analysis, streptokinase was found to increase the volume of pleural fluid drained from patients with organized empyemas, but there was no significant impact on hospital stay, defervescence, need for surgical intervention or mortality (de Souza et al., 2000). These observations provide a clinically-based rationale for the investigation of new interventional fibrinolysins for intrapleural use.

When bound to its receptor; uPAR (either on the cell surface or in soluble form), scuPA expresses enhanced and sustained fibrinolytic activity that is also relatively resistant to plasminogen activator inhibitors (PAI) (Higazi et al, 1996; Higazi, 1995; Manchanda, 1995). These properties suggest that use of this agent could be of advantage in organizing pleuritis, where the local concentrations of PAI are very high (Idell et al., 1991). The inventors have previously shown that pleural mesothelial cells and fibroblasts express uPAR and that uPAR is upregulated in these cells by cytokines expressed in pleural injury (Shetty and Idell, 1998; Shetty et al., 1996).

Based on the above, there is a need for methods and compositions that allow for the prevention of pleural adhesion formation.

SUMMARY OF THE INVENTION

The inventors have evaluated the ability of novel fibrinolytic strategies using either intrapleural recombinant human scuPA or scuPA pre-complexed to soluble recombinant uPAR (suPAR) to prevent pleural adhesion formation associated with pleural injury. While both agents were protective, the inventors found that protection due to scuPA against formation of intrapleural loculations in this model was virtually complete.

This application therefore relates to methods of preventing or decreasing the severity of scarring in a subject comprising: obtaining a pharmaceutical composition comprising scuPA or a scuPA mimetic; and administering the pharmaceutical composition to a subject; wherein scarring in the subject is either prevented or decreased relative to an amount of scarring that would be expected if the pharmaceutical composition were not administer to the subject.

The invention, in some specific regards, related to the prevention of pleural scarring, and in some even more specific regards, to the prevention of pleural scarring after an injury to the subject. Such pleural scarring often occurs following an injury to the lungs of a subject. For example, pneumonia, particulate-induced pleural injury, such as that induced by asbestos or other particulates, bleeding into the pleural space or immunologically-induced pleural injury such as that associated with collagen vascular diseases and chemically-induced pleural injury are all known to create the potential for scarring. Of course, the methods of the invention are not limited solely to the prevention of pleural scarring, and those of skill in the art will be able to modify, without undue experimentation, the methods taught herein to be able to test the ability of scuPA and scuPA-related compounds, such as scuPA mimetic, or mutated scuPA molecules to prevent any manner of scarring. Those of skill will further be able to employ the results of such testing to prevent any of a number of forms of scarring, for example, but not limited to acute lung injury and parenchymal lung scarring such as that associated with Acute (or Adult) Respiratory Distress Syndrome (ARDS), infectious, immunologically mediated or chemically or irradiation-induced pneumonitis, hyperoxia associated pneumonitis and particulate-induced lung scarring such as, for example, asbestosis or that induced by silica and interstitial lung diseases, including but not limited to idiopathic pulmonary fibrosis and sarcoidosis.

The pharmaceutical composition may be administered to the subject in any manner known to those of skill. In some preferred embodiments, the pharmaceutical composition is directly administered to a site in the subject. For example, the pharmaceutical composition may be delivered to the site of an existing or expected injury. In some cases, the pharmaceutical composition is administered intrapleurally. Those of ordinary skill will be able to determine appropriate routes, timing, and dosages of administration, in view of the teachings of this specification. In some cases, it will be appropriate to administer the pharmaceutical composition prior to the injury, for example, if the injury is elective or scheduled surgery, or the subject has a disease, such as pneumonia, that is expected to cause injury. In other cases, it will not be possible to administer the pharmaceutical composition prior to the injury, and the composition will be delivered after the injury.

In some instances, the scuPA or scuPA mimetic is bound to a scuPA receptor. The scuPA employed is some embodiments of the invention may be of any origin. For example, it may be of human origin. In some preferred embodiments, the scuPA is recombinant human scuPA. The scuPA may also be a modified scuPA. A "modified scuPA" is any molecule that has been modified away from a native scuPA configuration, but retains the anti-scarring benefits of scuPA. Modifications to scuPA may be made by any of a number of methods known to those of skill in the art, including known nucleic acid and polypeptide sequence modification techniques, such as site-specific mutagenesis. In some embodiments, the pharmaceutical composition will comprise a scuPA mimetic. A "scuPA" mimetic is a molecule that is designed to mimic the anti-scarring activity of scuPA. scuPA mimetics may be small molecules, modified polypeptides, and/or any other form of compounds known and producible by methods known to those of skill in the art. Those of skill will be able to prepare and test scuPA mimetic using the information concerning the activity of scuPA discloses herein.

The invention further contemplates methods of screening for compounds that prevent scarring comprising: obtaining a single chain urokinase plasminogen activator molecule (scuPA) or a scuPA mimetic as defined above; and testing for an ability of the scuPA or scuPA mimetic to prevent scarring. Such testing may comprise testing in a cultured cell, such as, for example, the cultured rabbit pleural mesothelial cell or lung fibroblast testing methods specifically detailed herein. Of course, those of skill will also be able to devise additional appropriate cell-based testing methods. Other testing methods will involve administering the scuPA or scuPA mimetic to a test animal, such as, for example, the test rabbits described herein. In some preferred embodiments, the test rabbits will have tetracycline induced pleural injury.

The invention also relates to modified scuPA and scuPA mimetics produced and then tested according to the methods disclosed herein.

In the context of the present document, including the claims, the words "a" and "an", when used with the conjunction "comprising" denote "one or more."

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Cleavage of fibrin clots by interventional agents in the presence of pleural fluids.

FIG. 2. Numbers of Adhesions in Rabbits treated with Intrapleural scuPA, scuPA bound to its Solubilized Receptor (scuPA-suPAR) or Control Vehicle (PBS). (‡) scuPA has fewer adhesions than PBS, $p<0.0001$, scuPA has fewer adhesions than scuPA-suPAR, $p=0.03$; (†) scuPA-suPAR has fewer adhesions than PBS, $p=0.004$.

DESCRIPTION OF ILLUSTRATIVE EMBODIMENTS

I. The Present Invention

Figure 3:
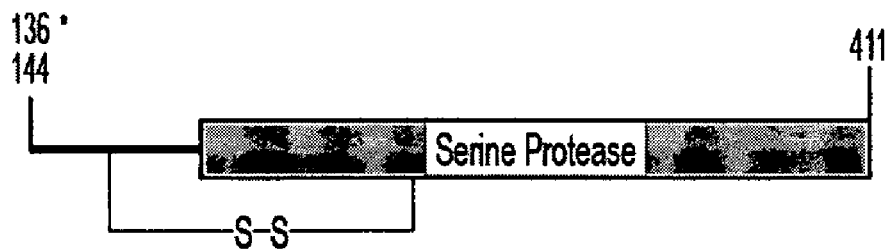
FIG. 3. Pleural Fluid Volume in Rabbits treated with Intrapleural scuPA, scuPA-suPAR or PBS.

Intrapleural loculation increases morbidity in pleural disorders such as hemothoraces or parapneumonic effusions. A fibrinous exudative phase precedes intrapleural adhesion formation between the visceral and parietal pleural surfaces. Therefore, the present inventions is based on single chain urokinase (scuPA) or scuPA bound to its receptor; and that suPAR, could prevent these adhesions based upon the relative resistance of these fibrinolysins to local inhibition by plasminogen activator inhibitors. The present invention is further based on scuPA in the prevention of pleural scarring after injury, for example lung injury. The present invention further relates to preventing any manner of scarring by employing scuPA and scuPA-related cmpounds, such as but not limited to scuPA mimetics, or mutated scuPA molecules.

The inventors found that recombinant human scuPA bound cultured rabbit pleural mesothelial cells or lung fibroblasts with kinetics similar to that reported for human cells; Kd of about 1 nM. ScuPA bound to suPAR maintained in vitro fibrinolytic activity in the presence of pleural fluids from rabbits with tetracycline (TCN)-induced pleural injury over 24 hr. In rabbits given intrapleural scuPA given 24 and 48 hr after intrapleural TCN, (n=10 animals) adhesion formation was prevented while scuPA complexed to its recombinant receptor; suPAR (n=12) attenuated adhesions compared to vehicle/TCN-treated rabbits (n=22, p≦0.005 versus controls in both cases). There were more adhesions in the scuPA-suPAR group than the scuPA group (p=0.02). Antigenic but not functional evidence of the interventional agents were detectable in pleural fluids at 72 hr after TCN. No local or systemic bleeding occurred due to either interventional agent. The data demonstrates that scuPA inhibits, while scuPA/suPAR attenuates adhesion formation in cases of pleural injury.

A. Urokinase Plasminogen Activator (uPA)

Urokinase plasminogen activator (uPA) is a serine protease and, when bound to its receptor, uPAR, initiates the activation of matrix metalloproteases (MMPs) as well as the conversion of plasminogen to plasmin (Coleman and Benach, 1999; Handley et al., 1986). These proteases confer on the cells the ability to degrade the extracellular matrix, thus allowing them to overcome the constraints of cell-cell and cell-matrix interactions (Handley et al., 1986). uPA and uPAR expression can be up-regulated by mitogen, growth factors, oncogenes, and ligation of integrin with extracellular matrix protein. It has been demonstrated that the uPA receptor is upregulated by stimuli that have been implicated in the pathogenesis of pleural injury and fibrosis including asbestos and the cytokines, TNF-α and TGF-β (Shetty and Idell, 1998; Perkins et al, 1999; Antony et al., 1995; Idell, 1995)

Several studies have indicated that uPA is released from many types of cultured cells as a single-chain proenzyme with little or no plasminogen activating capacity (Nielsen et al., 1988, Skriver et al., 1984, Eaton et al., 1984, Kasai et al., 1985, Pannell and Gurewich 1987). By limited proteolysis with catalytic amounts of plasmin, this proenzyme can be converted to its active two-chain counterpart.

uPAR was first identified on monocytes and cells of monocytic origin (Vassalli et al., 1985), and is a highly glycosylated 55- to 60-kDa protein (Ploug et al., 1998.). The uPAR molecule has three extracellular domains (D1-D3) and binds urokinase with high affinity via its receptor-binding domain, D1, which is located in the amino-terminal portion of the molecule. The functions of D2 and D3 have not been completely elucidated The uPA receptor binds active 54 kD uPA, but shows no binding of the low molecular weight (33 kD) form of active u-PA (Vassalli et al., 1985; Cubellis et al., 1986). Binding to the receptor does not require the catalytic site of uPA. Furthermore, the binding determinant of uPA has been identified in the amino-terminal part of the enzyme, in a region which in the primary structure is remote from the catalytic site. The receptor binding domain is located in the 15 kD amino-terminal fragment (ATF, residues 1-135) of the uPA molecule, more precisely within the cysteine-rich region, termed the growth factor region as this region shows homologies to the part of epidermal growth factor (EGF), which is responsible for binding to the EGF receptor. The amino acid residues which appear to be critical for binding are located within sequence 12-32 of uPA. (Appella et al., 1987).

Prourokinase, or urinary-type plasminogen activator, which is a naturally occurring plasminogen activator consisting of a single-chain polypeptide made up of 411 amino acids. Prourokinase is also referred to as single chain urokinase-plasminogen activator ("scuPA").

The light chain (amino terminal) of scuPA contains, in addition to an epidermal growth factor-like domain, a single kringle region that shows considerable homology with the kringles of tissue plasminogen activator (tPA). scuPA expresses little intrinsic plasminogen activator activity. scuPA can be activated by proteolytic cleavage to form a two-chain enzyme (tcuPA), which is susceptible to inhibition by plasminogen activator inhibitor type I (PAI-I). scuPA is also activated when it binds to its cellular receptor (uPAR), leading to a single chain molecule with less susceptibility to PAIs (Higazi et al., 1996), a property that could be of advantage in the setting of pleural inflammation scuPA is also resistant to irreversible inhibition by PAI-I as well as to other plasminogen activator-inhibitors. The resistance of scuPA to irreversible covalent bonds formation with PAI-1, appears to potentiate it's PA activity (Manchanda, 1995). Fibrin clots contain PAI-I derived from plasma and platelets and scuPA complexed to suPAR has been shown to be a potent fibrinolysin. scuPA complexed to suPAR was found to lyse fibrin clots more efficiently than equimolar amounts of scuPA alone, tcuPA or tcuPA bound to suPAR (Higazi et al., 1998).

Cleavage of scuPA occurs between residues Lys 158 and Ile 159 to form high molecular weight (HMW) two-chain urokinase and the catalytic site becomes susceptible to irreversible inhibition. Low molecular weight (LMW) two-chain urokinase derives from subsequent cleavage of the Lys 136-Lys 137 peptide bond and is readily inhibited by plasminogen activator-inhibitor ILMW uPA does not contain the amino terminal kringle, and as represented herein contains amino acids 164-411 of the mature sequence. Although it is only 14 amino acids longer than LMW two-chain urokinase, LMW uPA manifests fibrin selectivity identical to that of native, HMW scuPA, clearly excluding the kringle from a role in fibrin selectivity. In addition, LMW (32 kDa) uPA is susceptible to PAI-1.

II. Single Chain Urokinase Plasminogen Activator (scuPA) Nucleic Acids

The present invention employs human recombinant single chain urokinase plasminogen activator (scuPA) or scuPA pre-complexed to soluble recombinant uPAR (suPAR) to prevent pleuritis. In further embodiments, the present invention employs scuPA and scuPA-related compounds, such as but not limited to ascuPA mimetic, or a mutated scuPA molecule to prevent scarring.

A. scuPA Molecules

Important aspects of the present invention concern isolated DNA segments encoding wild-type, polymorphic or mutant scuPA proteins, polypeptides or peptides, comprising the sequence of SEQ ID NO:1, and biologically functional equivalents thereof.

The present invention concerns DNA segments, isolatable from mammalian cells, such as mouse or human cells, that are free from total genomic DNA and that are capable of expressing a protein, polypeptide or peptide that has scuPA activity. As used herein, the term "DNA segment" refers to a DNA molecule that has been isolated free of total genomic DNA of a particular species. Therefore, a DNA segment encoding scuPA refers to a DNA segment that contains wild-type, polymorphic or mutant scuPA coding sequences yet is isolated away from, or purified free from, total mammalian genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified scuPA gene refers to a DNA segment including scuPA protein, polypeptide or peptide coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and engineered segments that express, or may be adapted to express, proteins, polypeptides, domains, peptides, fusion proteins and mutants of scuPA encoded sequences.

"Isolated substantially away from other coding sequences" means that the gene of interest, in this case the scuPA gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments that encode a scuPA protein, polypeptide or peptide that includes within its amino acid sequence a contiguous amino acid sequence in accordance with, or essentially as set forth in, SEQ ID NO:2 and SEQ ID NO:3.

The term "a sequence essentially as set forth in SEQ ID NO:2 and SEQ ID NO:3" means that the sequence substantially corresponds to a portion of SEQ ID NO:2 and SEQ ID NO:3 and has relatively few amino acids that are not identical to, or a biologically functional equivalent of, the amino acids of SEQ ID NO:2 and SEQ ID NO:3.

The term "biologically functional equivalent" is well understood in the art and is further defined in detail herein. Accordingly, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of amino acids that are identical or functionally equivalent to the amino acids of SEQ ID NO:2 and SEQ ID NO:3 will be sequences that are "essentially as set forth in SEQ ID NO:2 and SEQ ID NO:3", provided the biological activity of the protein is maintained.

In certain other embodiments, the invention concerns isolated DNA segments that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO:1, and has relatively few codons that are not identical, or functionally equivalent, to the codons of SEQ ID NO:1. Again, DNA segments that encode proteins, polypeptide or peptides exhibiting scuPA activity will be most preferred.

The term "functionally equivalent codon" is used herein to refer to codons that encode the same amino acid, such as the six codons for arginine and serine, and also refers to codons that encode biologically equivalent amino acids. For optimization of expression of scuPA in human cells, the codons are shown in Table 1 in preference of use from left to right. Thus, the most preferred codon for alanine is thus "GCC", and the least is "GCG" (see Table 1 below). Codon usage for various organisms and organelles can be found on the internet at the Codon Usage Database website, allowing one of skill in the art to optimize codon usage for expression in various organisms using the disclosures herein. Thus, it is contemplated that codon usage may be optimized for other animals, as well as other organisms such as a prokaryote (e.g., an eubacteria, an archaea), an eukaryote (e.g., a protist, a plant, a fungi, an animal), a virus and the like, as well as organelles that contain nucleic acids, such as mitochondria or chloroplasts, based on the preferred codon usage as would be known to those of ordinary skill in the art.

TABLE 1

Preferred Human DNA Codons

| Amino Acids | | | Codons | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein, polypeptide or peptide activity where an amino acid sequence expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of nucleotides that are identical to the nucleotides of SEQ ID NO:1 will be sequences that are "essentially as set forth in SEQ ID NO:1".

One may also prepare fusion proteins, polypeptides and peptides, e.g., where the scuPA proteinaceous material coding regions are aligned within the same expression unit with other proteins, polypeptides or peptides having desired functions, such as for purification or immunodetection purposes (e.g., proteinaceous compostions that may be purified by affinity chromatography and enzyme label coding regions, respectively).

Encompassed by the invention are DNA segments encoding relatively small peptides, such as, for example, peptides of from about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 40, about 45, to about 50 amino acids in length, and more preferably, of from about 15 to about 30 amino acids in length; as set forth in SEQ ID NO:2 and SEQ ID NO:3 and also larger polypeptides up to and including proteins corresponding to the full-length sequences set forth in SEQ ID NO:2, and any range derivable therein and any integer derivable therein such a range.

In addition to the "standard" DNA and RNA nucleotide bases, modified bases are also contemplated for use in particular applications of the present invention. A table of exemplary, but not limiting, modified bases is provided herein below.

TABLE 2

Purine and Pyrmidine Derivatives or Analogs

| Abbr. | Modified base description |
|---|---|
| ac4c | 4-acetylcytidine |
| chm5u | 5-(carboxyhydroxylmethyl)uridine |
| Cm | 2-O-methylcytidine |
| Cmnm5s2u | 5-carboxymethylaminomethyl-2-thioridine |
| Cmnm5u | 5-carboxymethylaminomethyluridine |
| D | Dihydrouridine |
| Fm | 2'-O-methylpseudouridine |
| gal q | beta, D-galactosylqueosine |
| Gm | 2'-O-methylguanosine |
| I | Inosine |
| I6a | N6-isopentenyladenosine |
| m1a | 1-methyladenosine |
| m1f | 1-methylpseudouridine |
| m1g | 1-methylguanosine |
| m1I | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| Mam5u | 5-methylaminomethyluridine |
| Mam5s2u | 5-methoxyaminomethyl-2-thiouridine |
| Man q | Beta, D-mannosylqueosine |
| Mcm5s2u | 5-methoxycarbonylmethyl-2-thiouridine |
| Mcm5u | 5-methoxycarbonylmethyluridine |
| Mo5u | 5-methoxyuridine |
| Ms2i6a | 2-methylthio-N6-isopentenyladenosine |
| Ms2t6a | N-(9-beta-D-ribofuranosyl-2-methylthiopurine-6-yl)carbamoyl)threonine |
| Mt6a | N-(9-beta-D-ribofuranosylpurine-6-yl)N-methyl-carbamoyl)threonine |
| Mv | Uridine-5-oxyacetic acid methylester |
| o5u | Uridine-5-oxyacetic acid (v) |
| Osyw | Wybutoxosine |
| P | Pseudouridine |

TABLE 2-continued

Purine and Pyrmidine Derivatives or Analogs

| Abbr. | Modified base description |
|---|---|
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-(9-beta-D-ribofuranosylpurine-6-yl)carbamoyl)threonine |
| Tm | 2'-O-methyl-5-methyluridine |
| Um | 2'-O-methyluridine |
| Yw | Wybutosine |
| X | 3-(3-amino-3-carboxypropyl)uridine, (acp3)u |

III. scuPA Proteins, Polypeptides, and Peptides

The present invention also provides purified, and in preferred embodiments, substantially purified mammalian scuPA proteins, polypeptides, or peptides. The term "purified mammalian scuPA proteins, polypeptides, or peptides" as used herein, is intended to refer to an scuPA proteinaceous composition, isolatable from mammalian cells or recombinant host cells, wherein the scuPA protein, polypeptide, or peptide is purified to any degree relative to its naturally-obtainable state, i.e., relative to its purity within a cellular extract. A purified scuPA protein, polypeptide, or peptide therefore also refers to a wild-type or mutant scuPA protein, polypeptide, or peptide free from the environment in which it naturally occurs.

The scuPA proteins may be full length proteins, such as being 411 amino acids in length. The scuPA proteins, polypeptides and peptides may also be less then full length proteins, such as individual polypeptide, domains, regions or even epitopic peptides. Where less than full length scuPA proteins are concerned the most preferred will be those containing predicted immunogenic sites and those containing the functional domains identified herein.

Encompassed by the invention are proteinaceous segments of relatively small peptides, such as, for example, peptides of from about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 40, about 45, to about 50 amino acids in length, and more preferably, of from about 15 to about 30 amino acids in length; as set forth in SEQ ID NO:2 and SEQ ID NO:3, and also larger polypeptides of from about 51, about 52, about 53, about 54, about 55, about 56, about 57, about 58, about 59, about 60, about 65, about 70, about 75, about 80, about 85, about 90, about 95, about 100, about 110, about 120, about 130, about 140, about 150, about 160, about 170, about 180, about 190, about 200, about 220, about 240, about 260, about 280, about 300, about 320, about 340, about 360, about 380, about 400, about 420, up to and including proteins corresponding to the full-length sequences set forth in SEQ ID NO:2.

Generally, "purified" will refer to an scuPA protein, polypeptide, or peptide composition that has been subjected to fractionation to remove various non-scuPA protein, polypeptide, or peptide, and which composition substantially retains its scuPA activity, as may be assessed, assays described herein or would be known to one of skill in the art.

Where the term "substantially purified" is used, this will refer to a composition in which the scuPA protein, polypeptide, or peptide forms the major component of the composition, such as constituting about 50% of the proteinaceous molecules in the composition or more. In preferred embodiments, a substantially purified proteinaceous molecule will constitute more than 60%, 70%, 80%, 90%, 95%, 99% or even more of the proteinaceous molecules in the composition.

A peptide, polypeptide or protein that is "purified to homogeneity," as applied to the present invention, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Various methods for quantifying the degree of purification of scuPA proteins, polypeptides, or peptides will be known to those of skill in the art in light of the present disclosure. These include, for example, determining the specific proteinaceous molecule's activity of a fraction, or assessing the number of proteins, polypeptides and peptides within a fraction by gel electrophoresis. Assessing the number of proteinaceous molecules within a fraction by SDS/PAGE analysis will often be preferred in the context of the present invention as this is straightforward.

To purify an scuPA protein, polypeptide, or peptide a natural or recombinant composition comprising at least some scuPA proteins, polypeptides, or peptides will be subjected to fractionation to remove various non-scuPA components from the composition. In addition to those techniques described in detail herein below, various other techniques suitable for use in proteinaceous molecule purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Another example is the purification of an scuPA fusion protein using a specific binding partner. Such purification methods are routine in the art. As the present invention provides DNA sequences for scuPA proteins, any fusion protein purification method can be practiced.

The exemplary purification methods disclosed herein represent exemplary methods to prepare a substantially purified scuPA protein, polypeptide, or polypeptide. These methods are preferred as they result in the substantial purification of the scuPA protein, polypeptide or peptide in yields sufficient for further characterization and use. However, given the DNA and proteinaceous molecules provided by the present invention, any purification method can now be employed.

Although preferred for use in certain embodiments, there is no general requirement that the scuPA protein, polypeptide, or peptide always be provided in their most purified state. Indeed, it is contemplated that less substantially purified scuPA protein, polypeptide or peptide, which are nonetheless enriched in scuPA proteinaceous compositions, relative to the natural state, will have utility in certain embodiments. These include, for example, antibody generation where subsequent screening assays using purified scuPA proteinaceous molecules are conducted.

Methods exhibiting a lower degree of relative purification may have advantages in total recovery of proteinaceous molecule product, or in maintaining the activity of an expressed proteinaceous molecule. Inactive products also have utility in certain embodiments, such as, e.g., in antibody generation.

IV. Mutagenesis, Peptidomimetics and Rational Drug Design

It will also be understood that this invention is not limited to the particular nucleic acid and amino acid sequences of SEQ ID NO:1. Recombinant vectors and isolated DNA segments may therefore variously include these coding regions themselves, coding regions bearing selected alterations or modifications in the basic coding region, or they may encode larger polypeptides that nevertheless include such coding regions or may encode biologically functional equivalent proteins, polypeptides or peptides that have variant amino acids sequences.

The DNA segments of the present invention encompass biologically functional equivalent scuPA proteins, polypeptides, and peptides. Such sequences may arise as a consequence of codon redundancy and functional equivalency that are known to occur naturally within nucleic acid sequences and the proteinaceous compositions thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes designed by man may be introduced, for example, through the application of site-directed mutagenesis techniques as discussed herein below, e.g., to introduce improvements to the antigenicity of the proteinaceous composition or to test mutants in order to examine scuPA activity at the molecular level.

Site-specific mutagenesis is a technique useful in the preparation of individual peptides, or biologically functional equivalent proteins, polypeptides or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired proteinaceous molecule. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

As modifications and changes may be made in the structure of the scuPA genes, nucleic acids (e.g., nucleic acid segments) and proteinaceous molecules of the present invention, and still obtain molecules having like or otherwise desirable characteristics, such biologically functional equivalents are also encompassed within the present invention.

For example, certain amino acids may be substituted for other amino acids in a proteinaceous structure without appreciable loss of interactive binding capacity with structures such as, for example, antigen-binding regions of antibodies, binding sites on substrate molecules or receptors, or such like. Since it is the interactive capacity and nature of a proteinaceous molecule that defines that proteinaceous molecule's biological functional activity, certain amino acid sequence substitutions can be made in a proteinaceous molecule sequence (or, of course, its underlying DNA coding sequence) and nevertheless obtain a proteinaceous molecule with like (agonistic) properties. It is thus contemplated that various changes may be made in the sequence of scuPA proteins, polypeptides or peptides, or the underlying nucleic acids, without appreciable loss of their biological utility or activity.

Equally, the same considerations may be employed to create a protein, polypeptide or peptide with countervailing, e.g., antagonistic properties. This is relevant to the present invention in which scuPA mutants or analogues may be generated. For example, a scuPA mutant may be generated and tested for scuPA activity to identify those residues important for scuPA C activity. scuPA mutants may also be synthesized to reflect a scuPA mutant that occurs in the human population and that is linked to the development of cancer. Such mutant proteinaceous molecules are particularly contemplated for use in generating mutant-specific antibodies and such mutant DNA segments may be used as mutant-specific probes and primers.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein above for use in such embodiments, as well as for other uses, such as in the design of probes and primers and the like.

In terms of functional equivalents, it is well understood by the skilled artisan that, inherent in the definition of a "biologically functional equivalent" protein, polypeptide, peptide, gene or nucleic acid, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted.

In particular, where shorter length peptides are concerned, it is contemplated that fewer amino acids changes should be made within the given peptide. Longer domains may have an intermediate number of changes. The full length protein will have the most tolerance for a larger number of changes. Of course, a plurality of distinct proteins/polypeptide/peptides with different substitutions may easily be made and used in accordance with the invention.

It is also well understood that where certain residues are shown to be particularly important to the biological or structural properties of a protein, polypeptide or peptide, e.g., residues in binding regions or active sites, such residues may not generally be exchanged. In this manner, functional equivalents are defined herein as those peptides which maintain a substantial amount of their native biological activity.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a proteinaceous molecule is generally understood in the art (Kyte and Doolittle, 1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein, polypeptide or peptide thereby created is intended for use in immunological embodiments, as in certain embodiments of the present invention. U.S. Pat. No. 4,554,101, states that the greatest local average hydrophilicity of a proteinaceous molecule, as governed by the hydrophilicity of its adjacent amino acids, correlates with its immunogenicity and antigenicity, i.e., with a biological property of the proteinaceous molecule.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

In addition to the scuPA compounds described herein, it is contemplated that other sterically similar compounds may be formulated to mimic the key portions of the peptide structure. Such compounds, which may be termed peptidomimetics, may be used in the same manner as the peptides of the invention and hence are also functional equivalents.

Certain mimetics that mimic elements of proteinaceous molecule's secondary structure are described in Johnson et al. (1993). The underlying rationale behind the use of peptide mimetics is that the peptide backbone of proteinaceous molecules exists chiefly to orientate amino acid side chains in such a way as to facilitate molecular interactions, such as those of antibody and antigen. A peptide mimetic is thus designed to permit molecular interactions similar to the natural molecule.

Some successful applications of the peptide mimetic concept have focused on mimetics of -turns within proteinaceous molecules, which are known to be highly antigenic. Likely -turn structure within a polypeptide can be predicted by computer-based algorithms, as discussed herein. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of receptor modeling is now well known, and by such methods a chemical that binds scuPA can be designed and then synthesized. It will be understood that all such sterically designed constructs fall within the scope of the present invention.

In addition to the 20 "standard" amino acids provided through the genetic code, modified or unusual amino acids are also contemplated for use in the present invention. A table of exemplary, but not limiting, modified or unusual amino acids is provided herein below.

TABLE 3

Modified and Unusual Amino Acids

| Abbr. | Amino Acid |
| --- | --- |
| Aad | 2-Aminoadipic acid |
| Baad | 3-Aminoadipic acid |
| Bala | Beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |

TABLE 3-continued

Modified and Unusual Amino Acids

| Abbr. | Amino Acid |
|---|---|
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| aHyl | Allo-Hydroxylysine |
| 3Hyp | 3-Hydroxyproline |
| 4Hyp | 4-Hydroxyproline |
| Ide | Isodesmosine |
| aIle | Allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In one aspect, ay compound may be designed by rational drug design to function as a scuPA molecule. The goal of rational drug design is to produce structural analogs of biologically active compounds. By creating such analogs, it is possible to fashion drugs which are more active or stable than the natural molecules, which have different susceptibility to alteration or which may affect the function of various other molecules. In one approach, one would generate a three-dimensional structure for the scuPA protein of the invention or a fragment thereof. This could be accomplished by X-ray crystallography, computer modeling or by a combination of both approaches. An alternative approach, involves the random replacement of functional groups throughout the scuPA protein, polypeptides or peptides, and the resulting affect on function determined.

It also is possible to isolate a scuPA protein, polypeptide or peptide specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have enhanced and improved, or reduced, biological activity, for example, NO-dependent signal transduction, relative to a starting scuPA proteinaceous sequences. By virtue of the ability to recombinatly produce sufficient amounts of the scuPA proteins, polypeptides or peptides, crystallographic studies may be preformed to determine the most likely sites for mutagenesis and chemical mimicry. In addition, knowledge of the chemical characteristics of these compounds permits computer employed predictions of structure-function relationships. Computer models of various polypeptide and peptide structures are also available in the literature or computer databases. In a non-limiting example, the Entrez database (http://www.ncbi.nlm.nih.gov/Entrez/) may be used by one of ordinary skill in the art to identify target sequences and regions for mutagenesis.

V. Pharmaceutical Compositions and Delivery of scuPA

In an embodiment of the present invention, a method of treatment for a pleural disease by the delivery of a scuPA molecule is contemplated. Pleural diseases that are most likely to be treated in the present invention are those that result from injury to the lungs. In further embodiments, the present invention provides a method for the prevention of pleural scarring, as well as any manner of scarring. Pleural scarring often occurs following an injury to the lungs of a subject. For example, pneumonia, particulate-induced pleural injury, such as that induced by asbestos or other particulates, bleeding into the pleural space or immunologically-induced pleural injury such as that associated with collagen vascular diseases and chemically-induced pleural injury are all know to create the potential for scarring.

A. Injectable Compositions and Formulations scuPA and scuPA-related compounds of the present invention may be delivered in any method known to those of skill in the art. They may be preferably administered intrapleurally or nasally to a site of injury in a subject for the prevention of pleuritis. However, the pharmaceutical compositions disclosed herein may alternatively be administered parenterally, intravenously, intradermally, intramuscularly, transdermally or even intraperitoneally as described in U.S. Pat. No. 5,543,158; U.S. Pat. No. 5,641,515 and U.S. Pat. No. 5,399,363.

Injection of scuPA and scuPA-related compounds may be delivered by syringe or any other method used for injection of a solution, as long as the molecules can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, so rbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

B. Dosage and Schedules of Administration

The dosage of the active compound and dosage schedule may be varied on a subject by subject basis, taking into account, for example, factors such as the weight and age of the subject, the type of disease being treated, the severity of the disease condition, previous or concurrent therapeutic interventions, the manner of administration and the like, which can be readily determined by one of ordinary skill in the art.

Administration is in any manner compatible with the dosage formulation, and in such amount as will be therapeutically effective. The quantity to be administered depends on the subject to be treated, including, e.g., the capacity of the individual's immune system to synthesize antibodies, and the degree of protection desired. The dosage of the will depend on the route of administration and will vary according to the size of the host. Precise amounts of an active ingredient required to be administered depend on the judgment of the practitioner.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., innoculations) are also variable, but are typified by an initial administration followed by subsequent inoculation(s) or other administration(s).

In many instances, it will be desirable to have multiple administrations, usually not exceeding six administrations, more usually not exceeding four administrations and preferably one or more, usually at least about three administrations. Normally from two to twelve week intervals, more usually from three to five week intervals may be applicable.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods:

Induction of TCN-induced Pleural Injury. Female New Zealand white rabbits weighing 4 kg were used in this study. Briefly, freshly prepared intrapleural TCN with lidocaine 1 mg/ml was administered under sterile conditions into the right pleural space with the animal in the left lateral decubitus position using an 18 gauge×2", 2¼ mm ball stainless steel feeding needle inserted through a cutaneous subscapular incision made with a #10 scalpel, as the inventors previously described (Idell et al., 1998). Anesthesia was accomplished using intramuscular Ketamine and Xyline (Idell et al., 1998) and all animals were then carefully monitored throughout the preoperative period and postoperative periods to assure stability and the absence of overt pain or distress. The animals were sacrificed by administration of intravenous Euthasol after they were anesthetized using Ketamine and Xylazine at 72 hr after intrapleural TCN at which time they underwent direct inspection of the operative site, screening thoracic and abdominal autopsy, quantification of collection of pleural fluid and direct assessment of intrapleural adhesion formation. All animal protocols were approved by the Animal Research Committee of The University of Texas Health Center at Tyler and by the veterinarian WH), who periodically monitored the induction of anesthesia, procedures and preoperative animal welfare.

Preparation of Recombinant Human scuPA and scuPA-scuPAR Complexes. Soluble uPAR (suPAR) was expressed in *Drosophila* S2 cells (DES expression system, Invitrogen) and purified from S2 culture supernatants as previously described (Tarui et al., 2001). Wild-type human scuPA (aa1-411 of the mature human sequence) was also cloned and expressed using the DES system. SuPAR-S2 cells were expanded to a cell density of 20-30×10$^6$ cell/ml of culture media followed by the induction of expression using 0.5 mM $CuSO_4$ (final concentration). Culture supernatants were typically collected 5-7 days after induction. Supernatants were clarified by centrifugation, the pH of the supernatants was adjusted to pH 8.8 using 1M BICINE pH 9.0 and the media was sterile filtered through a 0.22 μm filter prior to purification. A column was prepared using SP-Sepharose (5×200 cm) and equililibrated with 20 mM BICINE pH 8.8 at 4° C. and the filtered supernatant was applied to this column at a flow rate of 2-5 ml/min. Typically, 2-5 L of supernatant was applied to this column at one time. The column was then washed with 20 mM BICINE pH 8.8 buffer (5 ml/min flow rate) until protein could no longer be detected in the flow through. A 0-0.5 M NaCl gradient was used to elute bound scuPA, which typically eluted between 0.1 and 0.2 M NaCl with >90% purity. Reverse phase HPLC (RP-HPLC) using a semipreparative $C_8$ column was used to polish the scuPA to a purity of >97%.scuPA prepared in this manner was active in complex with suPAR as well as when activated by plasmin and the specific activity was estimated to be 150,000 units/mg. S2-derived scuPA also bound to uPAR and suPAR with Kd similar to those reported for scuPA derived from natural and other recombinant sources.

Intrapleural Administration of Interventional Agents. At 24 and 48 hr after administration of intrapleural TCN, the animals were sedated with intravenous Domitor 1.5 mg/kg, after which they were placed in the prone position after which they were subjected to thoracentesis using a 21 gauge 1¼" needle on a 3 cc non-luer lock syringe containing a total volume of 1.1 ml of either scuPA, scuPA-suPAR or the phosphate buffered saline, pH 7.4 vehicle. Entry into the pleural space was confirmed by initial aspiration of a small amount of pleural fluid, after which the contents of the syringe was injected into the pleural space. In pilot studies, the inventors determined that this procedure was more practical than imaging of the pleural effusion by intraoperative ultrasonography, followed by direct aspiration. The animals received a dose of 0.5 mg/ml of either interventional agent, or a total dose of 2 mg of interventional agent at each of the two intrapleural administrations at 24 and 48 hr post-TCN. The duration of sedation approximated 20-30 minutes and the animals appeared to tolerate the repeated episodes of sedation without distress or apparent change in behavior.

Collection and Processing of Pleural Fluid and Blood Samples. Pleural fluids were immediately collected using a 60 ml plastic syringe after the right and left hemithoraces were inspected. The total pleural fluid volume was measured and a sample was collected in 0.9% citrate and placed on ice. Samples of the citrated fluids were used to determine the total red and white blood cell counts using a Coulter counter (Beckman Coulter Inc., Hialeah, Fla.) and slides were prepared for differential white cell counts. Pleural fluid total protein and lactate dehydrogenase (LDH) determinations were done, as the inventors previously described (Idell et al., 1998). Blood from an ear vein was also collected and placed in citrate immediately before administration of intrapleural TCN and again immediately before sacrifice by administration of intravenous Euthasol. Aliquots were used to determine the red and white cell counts, as well as differential white blood cell analyses.

Incidence of Extrapleural Administration of TCN. 13 of 57 rabbits in this study were not evaluable because of extrapleural administration of the TCN. The incidence of misplaced sclerosant was comparable in the three treatment groups. Extrapleural delivery of TCN was confirmed by autopsy analysis. These animals had apparent mediastinal or intrahepatic delivery of the sclerosant. 7/29 animals in the TCN-PBS group had extrapleural TCN administration. 6/28 animals in the interventional groups; 4 in the scuPA group and 2 in the scuPA-suPAR group, had similar extrapleural administration of autopsy-confirmed extrapleural TCN. The proportion of non-evaluable animals did not differ between any of the groups, indicating the absence of statistic bias attributable to the error rate associated with the procedure used to induce pleural injury (p=0.64).

Post-mortem Intrapleural Adhesion Assessment. Pleural adhesions were quantitated by direct inspection of the right hemithorax after removal of all pleural fluid that could be harvested. In cases where florid adhesion formation filled the hemithorax and trapped the lung, the adhesions were designated as too numerous to count. Where adhesion formation was more limited, as was typically the case in the animals that received the interventional agents, the number of discrete adhesions between the visceral and parietal pleural surfaces was counted.

Binding of Human Recombinant scuPA to Cultured Rabbit Pleural Mesothelial Cells and Rabbit Lung Fibroblasts. Rabbit pleural mesothelial cells and lung fibroblasts were isolated from rabbit pleural tissues as the inventors previously described and were grown to confluence in RPMI medium, as the inventors previously described (Shetty and Idell, 1998). Competition binding studies were carried out using these cells and $^{125}$I, scuPA. Briefly, mesothelial cells and fibroblasts were plated in 24-well plates (25,000 cells/well) and cultured overnight at 37° C./5% $CO_2$. Cells were briefly exposed to acidic conditions (0.5M glycine 100 nM NaCl pH 3.0, 3 min at room temperature) to remove endogenously bound rabbit uPA, then washed 3× with PBS buffer. $^{125}$I scuPA (1 nM) was added to each well either alone or in the presence of increasing concentrations of cold scuPA. After 2 hrs. of incubation at room temperature, the cells were washed using PBS (3×) followed by dissolution in 1 N NaOH. Each well was then aspirated and the contents were placed into individual 12×75 mm tubes for analysis using a γ-counter.

Lysis of Radiolabeled Clots by scuPA or a scuPA/suPAR in the Presence of Rabbit Pleural Fluids. The ability of the interventional agents to lyse fibrin clots in the presence of pleural fluids was assessed by radioassay, as the inventors previously reported (Higazi et al., 1998). Human fibrinogen was radiolabeled with $^{125}$I-labeled fibrinogen which was added, in separate experiments, to 3 randomly selected pleural fluids from rabbits challenged with intrapleural TCN (1 collected at 24 hr post TCN and 2 others at 72 hr post-TCN) (final concentration 60,000 cpm/150 μl). Plasminogen-depleted human fibrinogen was added to a final concentration of 2 mg/ml, $CaCl_2$ to a final concentration of 10 nM and human thrombin to a final concentration of 0.2 U, after which the mixtures were immediately placed in polyethylene tubes in aliquots of 150 μl and the total radioactivity counted using a γ counter. Radiolabeled fibrin clots were then allowed to form as the mixtures were incubated at room temperature for 1 hr. scuPA-suPAR or two-chain uPA; tcuPA—suPAR complexes by adding equal volumes of 1 μM concentrations of either scuPA or tcuPA with 1 μM suPAR. The complexes were allowed to form by incubation at room temperature for 5 min and then immediately added to a mixture of 150 μl of clot and 300 μl of PBS. 30 μl of scuPA, tcuPA or either scuPA-suPAR or tcuPA-suPAR complexes or control supplemental suPAR alone (each 500 nM) were then added to each tube (final concentration 50 nM). The radioactivity of 10 μl of clot lysate was then measured at 1, 2, 4, 6, 7, 8, 10 and 24 hr using a γ counter.

Pleural Fluid Coagulation and Fibrinolytic Analyses. Pleural fluid procoagulant activity was determined by its ability to shorten the recalcification time of normal pooled human plasma, as the inventors previously reported (Strange et al., 1995). Antigenic determination of pleural fluid uPA was performed by ELISA assay (American Diagnostics #894, Greenwich, Conn.) that recognizes human free uPA, uPA complexed to PAI or uPA in complex with uPAR. Antigenic determination of soluble uPAR was likewise determined by ELISA assay (American Diagnostics, #893). Pleural fluid and plasma D-dimer was determined by a rapid latex agglutination slide test using mouse monoclonal antibodies (Diagnostica Stago, Asnieres-sur-Seine, France), as the inventors previously reported (Strange et al., 1995). Pleural fluid PA activity was assessed using two independent methods. The PA activity of pleural fluid samples (4 TCN-PBS, 1 TCN scuPA and 5 TCN-scuPA-suPAR-treated animals) was first assayed based upon amidolytic activity using the Spectrolyse PA/PAI activity assay kit (American Diagnostica #452). The inventors also performed fibrin enzymography to evaluate the presence of functional uPA in pleural fluids and reverse fibrin enzymography to evaluate the presence of functional PA inhibitor activity as previously described (Strange et al., 1995).

Statistics. Nonparametric analyses of variables including pleural fluid variables and adhesions were chosen as these variables are not known to be normally distributed. Intragroup variation was first determined by Kruskal Wallis one-way analysis of variance. Specific comparisons of variables between groups was performed using the Mann Whitney U-Wilcoxon rank sum W test. Fishers exact probability was used to compare the variables for selected two-group comparisons.

Example 2

Cleavage of Fibrin Clots by Interventional Agents in the Presence of Rabbit Pleural Fluids. Of the agents tested, only scuPA-suPAR complexes demonstrated ability to lyse fibrin clots at early (6 h) as well as at late (20 hr) intervals in the presence of pleural fluids from TCN-treated rabbits (FIG. 1). As expected, scuPA or tcuPA alone did increase release of radiolabeled fibrin versus the control release of the nucleotide in the presence of suPAR. Cleavage of radiolabeled fibrin by tcuPA complexed to suPAR was not detectable early (6 h) but was detectable at 20 h after its addition to radiolabeled clot in the presence of rabbit pleural fluid.

Example 3

Binding of radiolabeled uPA to rabbit pleural mesothelial cells and lung fibroblasts. scuPA bound to both rabbit mesothelioma cells and fibroblasts with a Kd estimated to be 5-10 nM in both instances. These kinetics were similar to the Kd of scuPA (0.2-4 nM) previously reported in various human cell systems (Mazar et al., 1999).

Example 4

Detection of Interventional Agents in Pleural Fluids. The inventors confirmed the intrapleural delivery of the interventional agents by direct aspiration of pleural fluid immediately prior to injection of the agents or control vehicle. The ability to aspirate fluids at 24 and 48 h after intrapleural TCN confirms the previously reported findings in this model; that pleural fluids begin to form by 24 h and then enlarge with extensive formation of adhesions by 72 h post-TCN (Idell et al., 1998; Strange et al., 1995). The inventors assayed 21/22 pleural fluids from the TCN-PBS treated control animals for the presence of antigenic human uPA and soluble uPAR and could not detect either protein. The inventors also tested the pleural fluids of 3 naïve animals that received intrapleural TCN but no subsequent intrapleural injections and likewise found no detectable levels of uPA or uPAR. All 10 of the scuPA-treated animals had detectable levels of this agent (median: 11 ng/ml, range: 3-31 ng/ml). 11/12 of the scuPA-suPAR-treated animals likewise contained detectable amounts of uPA, likely reflecting the reported ability of the assay to detect human uPA bound to uPAR (median: 17 ng/ml, range: 2-75 ng/ml). Soluble uPAR was detectable in 11/12 pleural fluid samples from the suPA-suPAR-treated animals (median: 21 ng/ml, range 0-24 ng/ml). The data therefore confirm that the recombinant human interventional agents could be detected in the appropriate interventional groups at 24 h after the last intrapleural dose was given; at 48 h post-TCN.

The inventors could not detect increased PA activity by amidolytic assay in the TCN-PBS pleural fluids, nor was pleural fluid PA activity detectable in the TCN-scuPA or TCN-scuPA-suPAR fluids using this technique. By reverse fibrin enzymography, the inventors found that these pleural fluids contained a zone of PA inhibitor activity that could be neutralized by an antibody to PAI-1, confirming the presence of this inhibitor within these fluids, as the inventors previously reported in this model (Strange et al., 1995). By fibrin enzymography, the inventors found that most of the fibrinolytic zones related to uPA or tPA bound to PAI, as the inventors previously reported (Strange et al., 1995). uPA-like activity, which comigrated with the human uPA standard, was usually not detected: these zones were identified in 2 of 9 randomly selected TCN-PBS pleural fluid samples, in 1/9 TCN-scuPA samples and in 3/9 TCN-scuPA-suPAR samples.

The presence of detectable levels of human uPA related antigen in the fluids of rabbits treated with scuPA alone or in complex with suPAR 24 hr after intrapleural administration further suggests that the agents remained localized in the pleural space. Improved protection afforded by scuPA alone suggests the possibility that binding to endogenous receptor may be preferable to administration of preformed scuPA-suPAR complexes. Alternatively, the apparent superiority of the scuPA alone could reflect the 2-fold molar relative excess of scuPA alone versus that in complex, since both agents in this trial were administered at the same intrapleural dosage and the suPAR moiety accounted for half of the administered complex.

Example 5

Analysis of Intrapleural Adhesion Formation. The typical extensive intrapleural organization, with visceral parietal pleural that were too numerous to count, was observed in 18/22 of the TCN/intrapleural PBS control animals (FIG. 1). This appearance was identical to that the inventors observed in the naïve controls that received intrapleural TCN but no subsequent intrapleural injections (n=3), indicating that the two subsequent thoracenteses of PBS did not appreciably affect the development of intrapleural adhesions in this model. In 4 TCN/intrapleural PBS animals, a pleural effusion but no adhesions were observed. In these instances, it is likely that the TCN was delivered into the proximate soft tissues of the chest wall, since no other site of delivery could be identified at post-mortem examination. These a typical control animals were included in the statistical comparisons with the animals treated with the intrapleural interventions, since the inventors could not exclude the possibility that the intrapleural administration of PBS the control vehicle might alter the development of TCN-induced pleural injury in individual animals.

In the TCN-scuPA group, 9/10 animals had no adhesions in the right pleural space; ipsilateral to the previously administered TCN (FIG. 2). One animal in this group had two discrete apical adhesions present in the right pleural space. The TCN-scuPA group demonstrated significantly fewer adhesions than the control TCN-PBS group (p<0.001).

In the TCN-scuPA-suPAR group, 5/12 animals had no adhesions in the right pleural space (FIG. 2). 6/12 animals in this group had 1-5 discrete adhesions.1 animal in this group had extensive adhesions, resembling the response typically seen in the TCN-PBS-treated animals. The TCN-scuPA-suPAR group had significantly fewer than the control TCN-PBS group (p=0.004) but more adhesions than the TCN-scuPA group (p=0.02). When both interventional groups combined were compared to the control group, the TCN-PBS controls were found to have more adhesions (p<0.0001).

In the PBS-TCN group, the right lung was, in all cases restricted from full inflation by the intrapleural adhesions and was dusky. The contralateral (left) lung in all cases was pink and fully expanded. In animals treated with the intrapleural interventional agents, the right lung was often of a purplish hue, even in the absence of extensive adhesions, likely reflecting the presence of a chemical pneumonitis induced by TCN and atelectasis, as the inventors previously reported (Miller et al., 1999).

Example 6

Pleural Effusion Volumes. Right pleural effusions ipsilateral to the previously administered intrapleural TCN were identified in all animals at 72 hr post induction of pleural injury (FIG. 3; Table 4). These effusions generally appeared to be sanguinous and were carefully suctioned from the right hemithorax so as to permit assessment of the extent of visceral-parietal adhesion formation, as noted above. Rarely, small serous left pleural fluid collections occurred in association with the large right pleural effusions. For all groups combined, the median volume of right pleural fluid at 72 hr post-TCN was 34 ml (range: 10-53 ml), comparable to the previously reported observations Idell et al., 1998). The median amount of right-sided pleural fluid in the TCN-PBS group was 27 ml (range 14-40 ml). In the TCN-scuPA group, the median right pleural effusion was 38 ml (10-50 ml), while in the TCN scuPA-suPAR animals, the median was 40.5 ml (17-53 ml). The trend towards lesser amounts of pleural fluid in the TCN-PBS controls did not achieve statistical significance (p=0.07).

TABLE 4

Pleural Fluid Cellular and Bilochemical Parameters

|  | PBS (control) | | | scuPA | | | scuPA + suPAR | | |
| --- | --- | --- | --- | --- | --- | --- | --- | --- | --- |
|  | Mean | Median | Range | Mean | Median | Range | Mean | Median | Range |
| Pleural Fluid WBC* | 3.91 | 2.64 | 10.0 | 10.61 | 6.07 | 36.32 | 6.51 | 5.78 | 11.48 |
| Pleural Fluid PMN % | 16 | 13 | 42 | 30 | 17 | 82 | 38 | 38 | 56 |
| Pleural Fluid Lyniph % | 14 | 11 | 61 | 8 | 11 | 14 | 8 | 7 | 8 |
| Pleural Fluid MacMono % | 69 | 75 | 84 | 61 | 77 | 66 | 53 | 55 | 64 |
| Pleural Fluid Neutrophil Count* | .56 | .50 | 1.65 | 3.14 | 1.25 | 13.24 | 2.20 | 2.07 | 6.03 |

TABLE 4-continued

| | Pleural Fluid Cellular and Bilochemical Parameters | | | | | | | | |
|---|---|---|---|---|---|---|---|---|---|
| | PBS (control) | | | scuPA | | | scuPA + suPAR | | |
| | Mean | Median | Range | Mean | Median | Range | Mean | Median | Range |
| Pleural Fluid Protein (nig/mI) | 42.8 | 41.5 | 14.3 | 41.8 | 42.6 | 20.2 | 42.6 | 41.9 | 14.8 |
| Pleural Fluid LDH (IU/ml) | 210 | 147 | 565 | 194 | 123 | 699 | 223 | 213 | 324 |
| Pleural Fluid NPP (sec) | 309.5 | 290.1 | 291.8 | 312.7 | 292.9 | 340.9 | 260.8 | 242.2 | 344.3 |

*Cell count shown represent data × $10^6$ cells. Pleural fluid total white blood cell (WBC) counts and differential cell counts are shown. PMN: neutrophils, Lyniph: lymphocytes, Mac/mono: macrophages/monocytes. LDH; lactate dehydrogenase in International Units (IU)/ml, NPP: Pleural fluid recalcification times expressed in seconds (sec). Differences in the data from the groups are discussed in the text of the results and additional analyses are provided below.

Example 7

Figure 4:
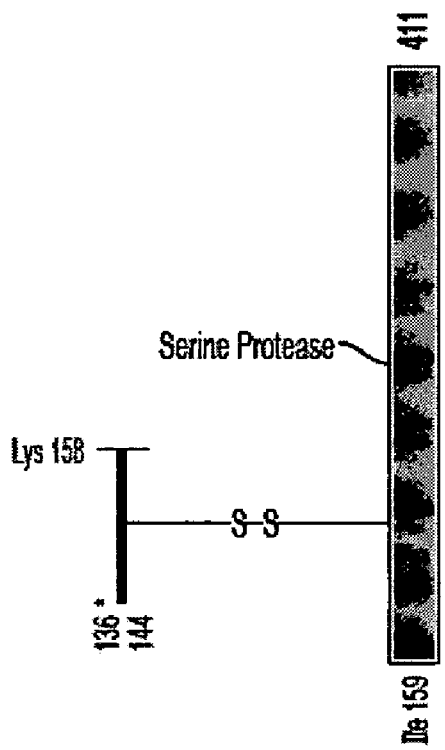
FIG. 4. Total Protein Concentration in Pleural Fluids from Rabbits Treated with Intrapleural scuPA, scuPA-suPAR or PBS.
Figure 5:
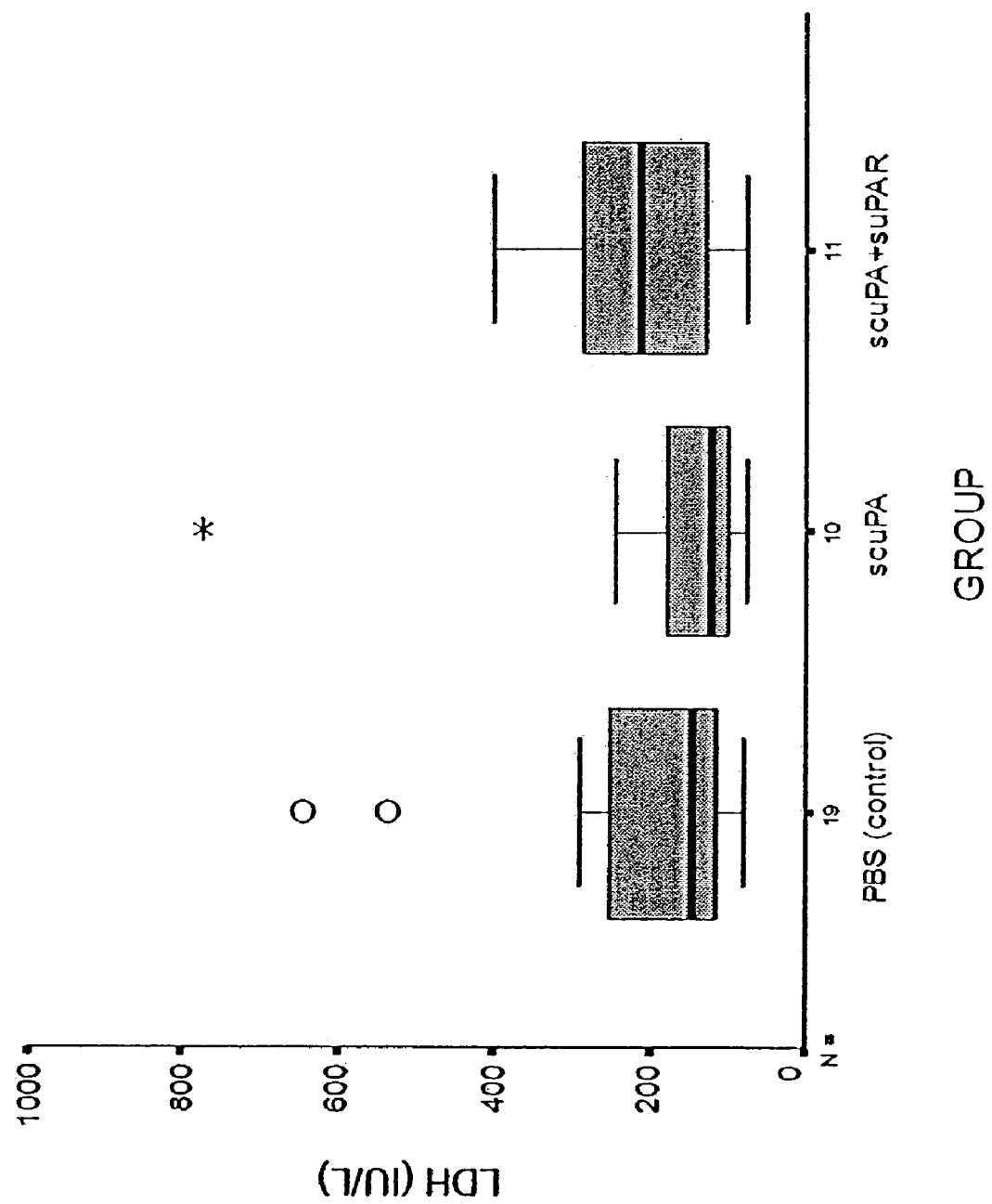
FIG. 5. Lactate Dehydrogenase (LDH) Concentrations in Pleural Fluid of Rabbits treated with scuPA, scuPA-suPAR or PBS.

Pleural Fluid Cell Counts and Biochemical Parameters. The pleural fluid total protein (FIG. 4) and LDH concentrations (FIG. 5) were measured as general indices of the local inflammatory response. The pleural fluid total protein concentration was nearly identical in all groups: TCN-PBS median 41.5 mg/ml versus TCN-scuPA 42.6 mg/ml and TCN-scuPA-suPAR 43.3 mg/ml, nor was there any difference in total protein concentrations between the TCN-PBS and naïve controls (p=0.23). There were likewise no significant differences in the concentrations of pleural fluid LDH between the groups (p=0.37), nor between the TCN-PBS group and naïve controls (p=0.53). In the TCN PBS group, the median concentration of LDH in pleural fluid was 147 IU/L, while that of the TCN-scuPA group was 120 IU/L and that of the TCN scuPA-suPAR group was 210 IU/L. See Table 4.

Figure 6:
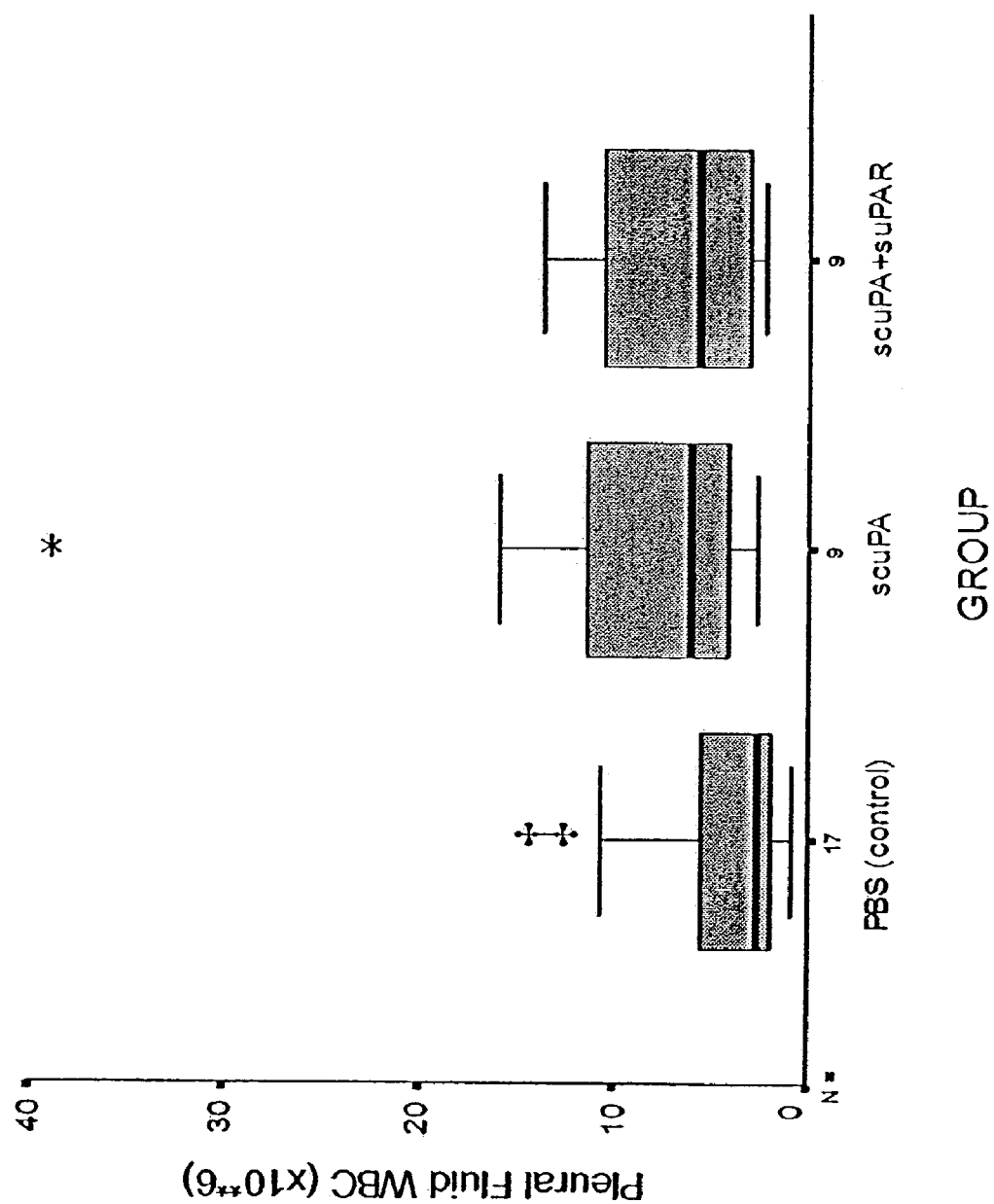
FIG. 6. Total White Blood Cells (WBC) in Pleural Fluids of Rabbits Treated with scuPA, scuPA-suPAR or PBS. (‡) PBS group is lowest, $p=0.04$.
Figure 7:
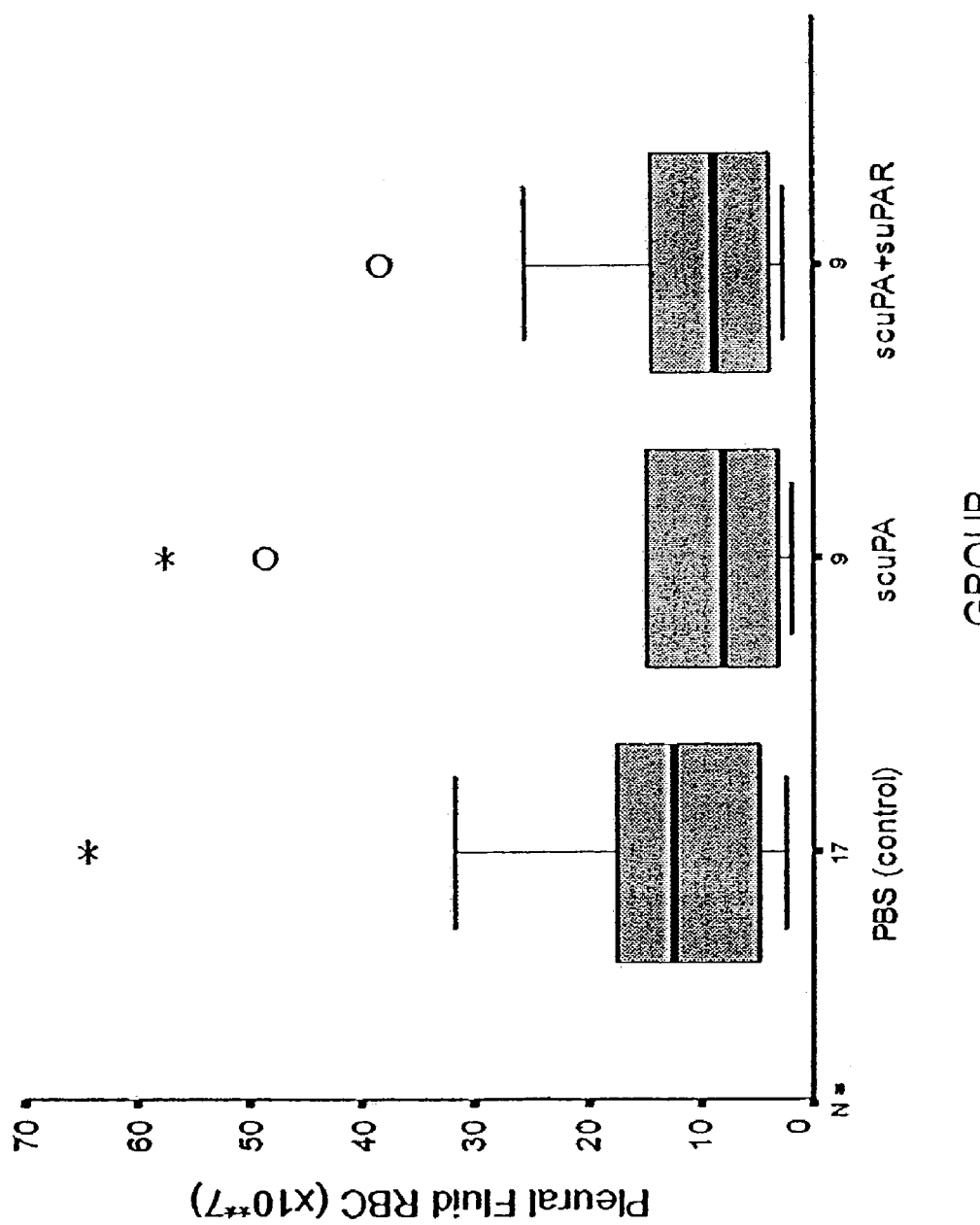
FIG. 7. Total Red Blood Cell Counts (RBC) in Pleural Fluids of Rabbits Treated with scuPA, scuPA-suPAR or PBS.
Figure 8:
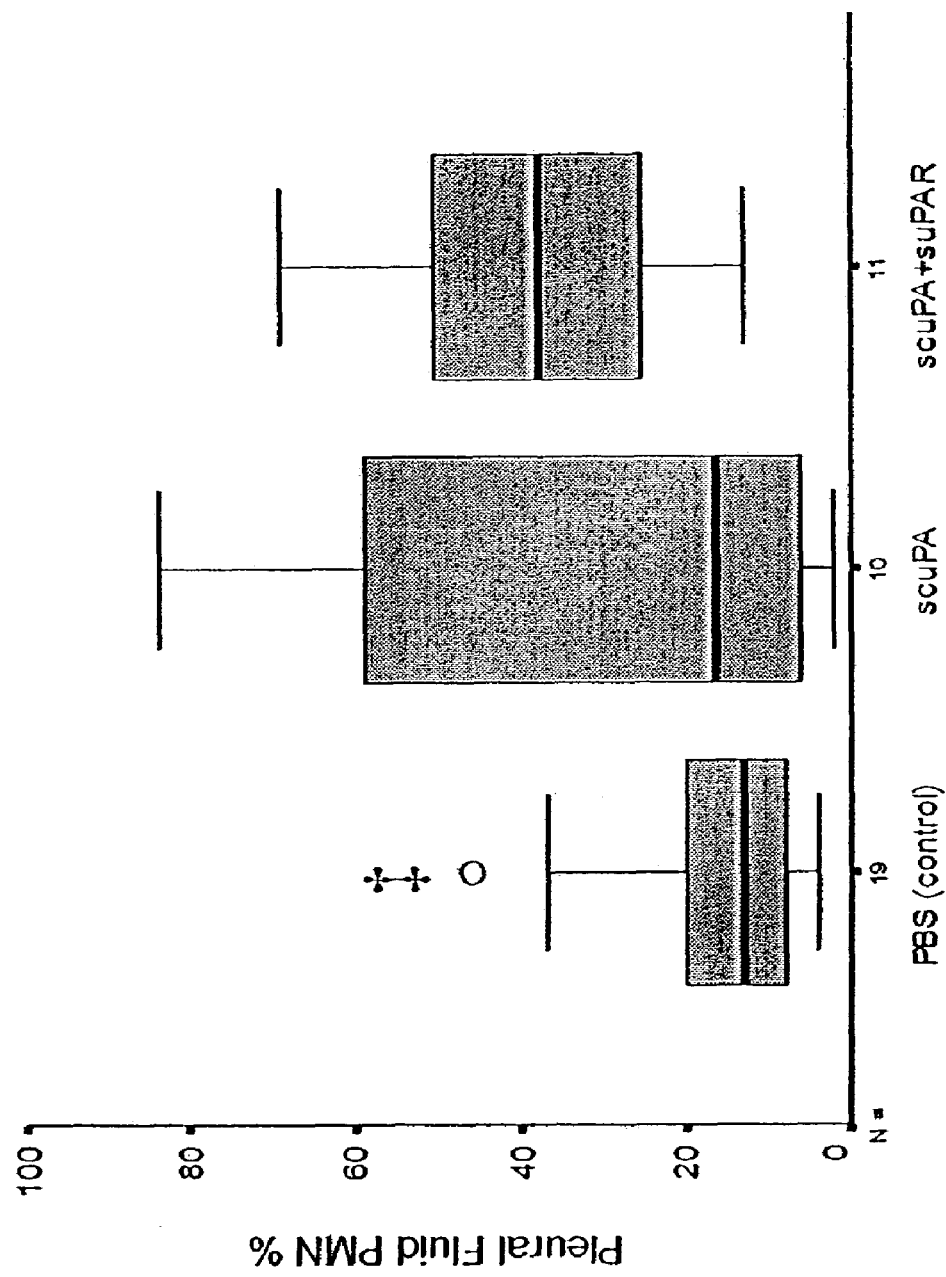
FIG. 8. The Percentage of Neutrophils (PMN) in Pleural Fluids of Rabbits Treated with scuPA, scuPA-suPAR or PBS. (‡) PBS group is lowest $p=0.01$.
Figure 9:
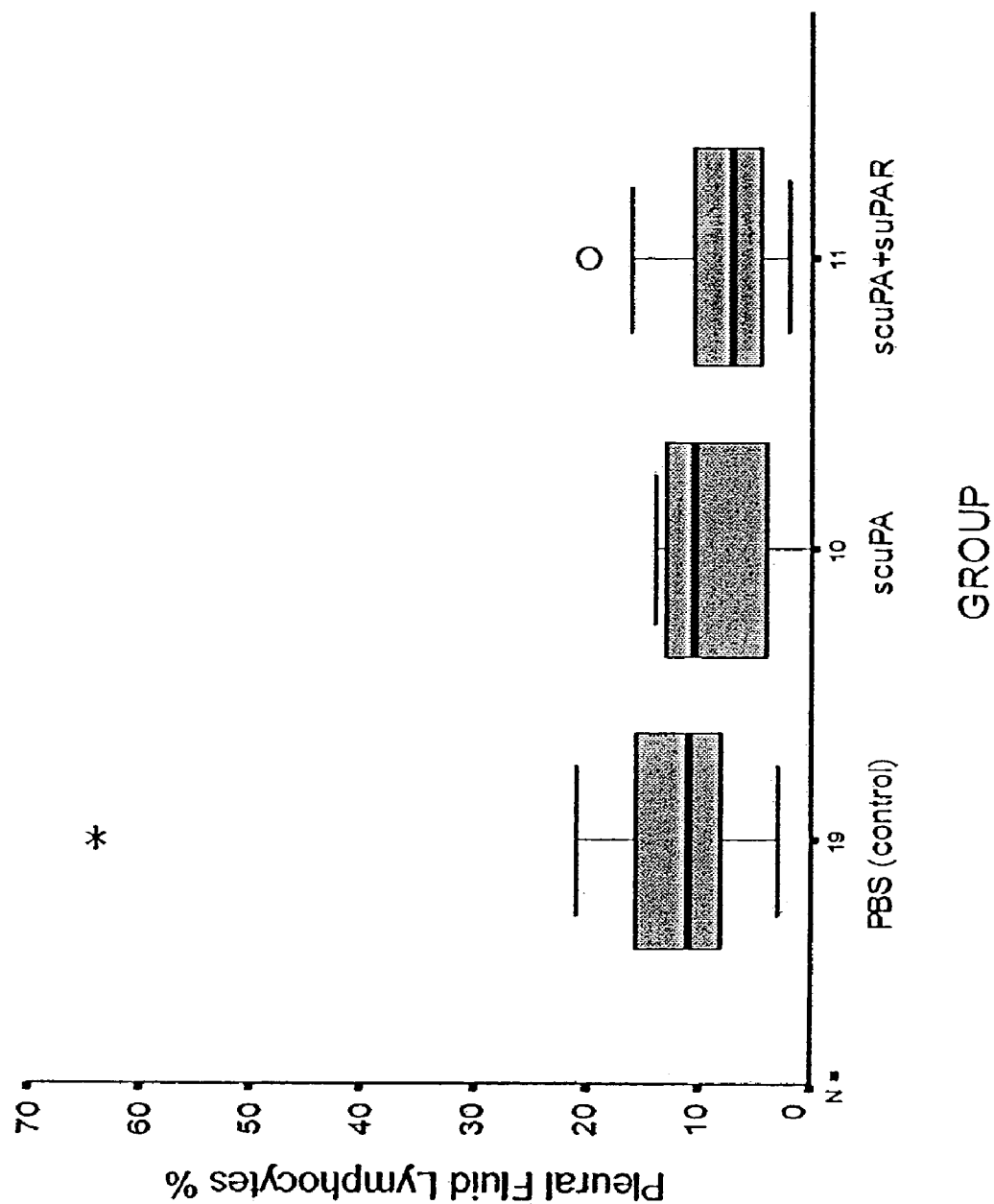
FIG. 9. The Percentage of Lymphocytes in Pleural Fluids of Rabbits Treated with scuPA, scuPA-scuPAR or PBS.
Figure 10:
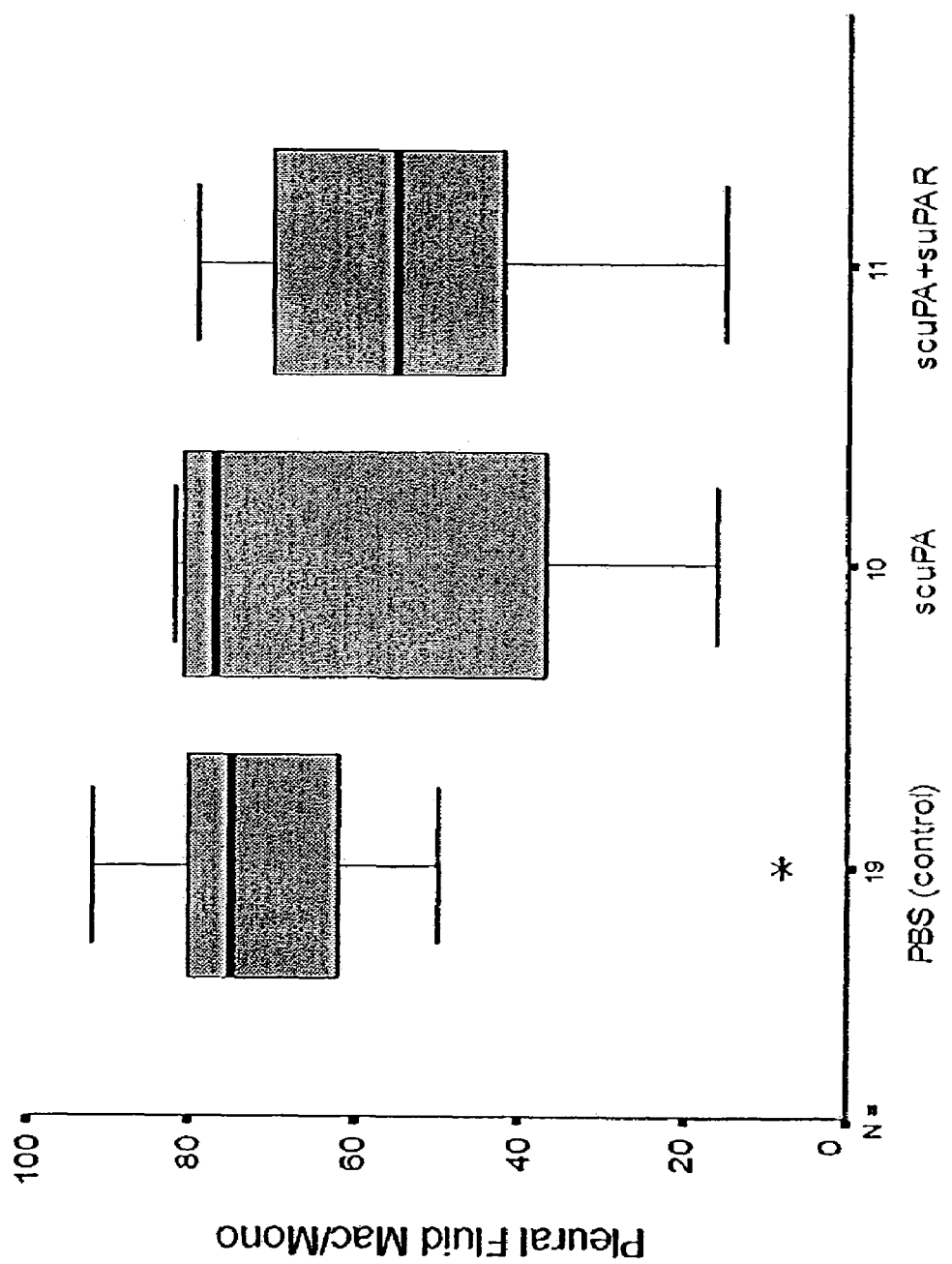
FIG. 10. The Percentage of Monocytes/Macrophages in Pleural Fluids Treated with scuPA, scuPA-suPAR or PBS.

The median pleural fluid total white blood cell count was $2.64 \times 10^6$ cells/ml in the TCN-PBS group, $6.07 \times 10^6$ cells/ml in the TCN-scuPA group and $4.42 \times 10^6$ cells/ml in the TCN scuPA-suPAR group, values comparable to those the inventors previously reported in the model (Miller et al., 1999) (FIG. 6). The total WBC counts were significantly lower in the TCN-PBS group (p=0.04), but there was no difference between the other interventional groups. There were also no significant differences between the TCN-PBS group and the naïve controls (p=0.15). The median RBC count in the TCN-PBS group was $12.4 \times 1$ cells/ml versus $8.0 \times 10^7$ cells/ml in the TCN-scuPA group and $6.4 \times 10^7$ cells/ml in the scuPA-suPAR group (FIG. 7). The total red cell (RBC) counts in the three groups did not differ significantly (p=0.73), attesting to the absence of intrapleural bleeding due to local administration of the fibrinolytic agents. There were also no significant differences in the pleural fluid RBC counts in the TCN-PBS group and the naïve controls (p=0.71), suggesting that the additional thoracenteses to which all experimental groups were subjected did not cause appreciable local bleeding. On differential WBC analyses, the percentage of neutrophils (PMN) observed in the TCN-PBS group (medianp: 12%, range 4-46%) was significantly lower than that of the other groups (p=0.01) (FIG. 8; Table 5). Modestly increased levels were seen in the TCN-scuPA group (median 14%, range 2-84%), while in the TCN-scuPA-suPAR group, a median of 35% PMN (range: 13-60%) was observed. There was no significant difference in the percentages of lymphocytes or macrophages/monocytes present in the pleural fluids of the different groups (p=0.22 and 0.08, respectively) (FIG. 9, FIG. 10). Mesothelial cells were rarely seen on differential cell counts.

TABLE 5

| | Pleural Fluid and Peripheral Blood Iotal Neutrophil Counts | | | | | |
|---|---|---|---|---|---|---|
| | Pleural Fluid | | Peripheqal Blood Before Rx | | Peripheral Blood After Rx [1] | |
| | Median | Mean | Median | Mean [1] | Median | Mean |
| PBS | .56 | .50 | 1.36 | 1.33 | 1.24 | 1.23 |
| scuPA | 3.14 | 1.25 | 2.01 | 2.04 | 1.80 | 1.70 |
| scuPA + suPAR | 2.20 | 2.07 | 2.45 | 2.55 | 1.36 | 1.33 |

[1] Neutrophil counts shown represent $10^6$ cells. Peripheral blood Before Rx: neutrophils in peripheral blood obtained before administration of intrapleural treatments. Peripheral Blood After Rx:

Example 8

Figure 11:
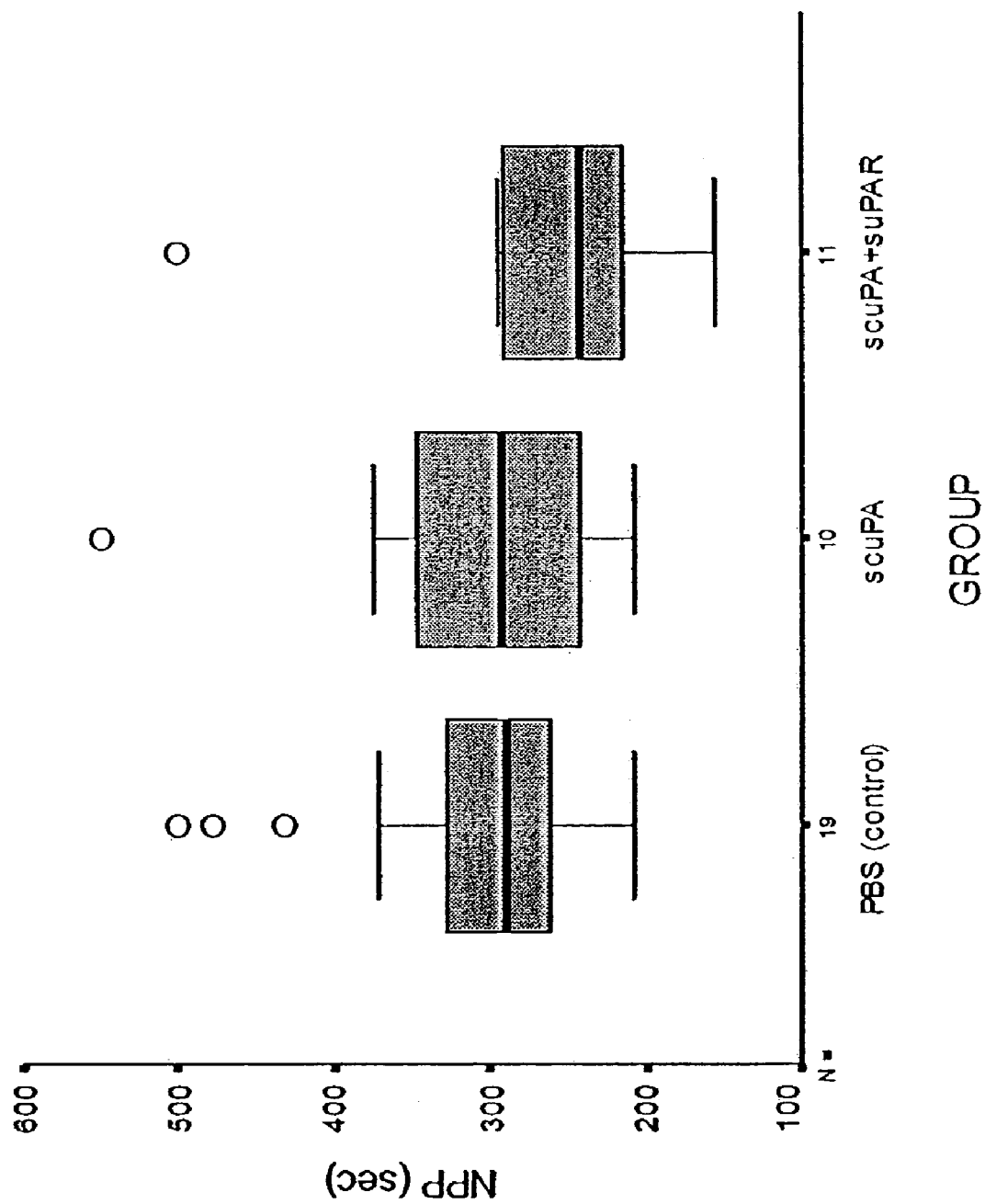
FIG. 11. Recalcification times of Pleural Fluids from Rabbits Treated with scuPA, scuPA-suPAR or PBS.
Figure 12:
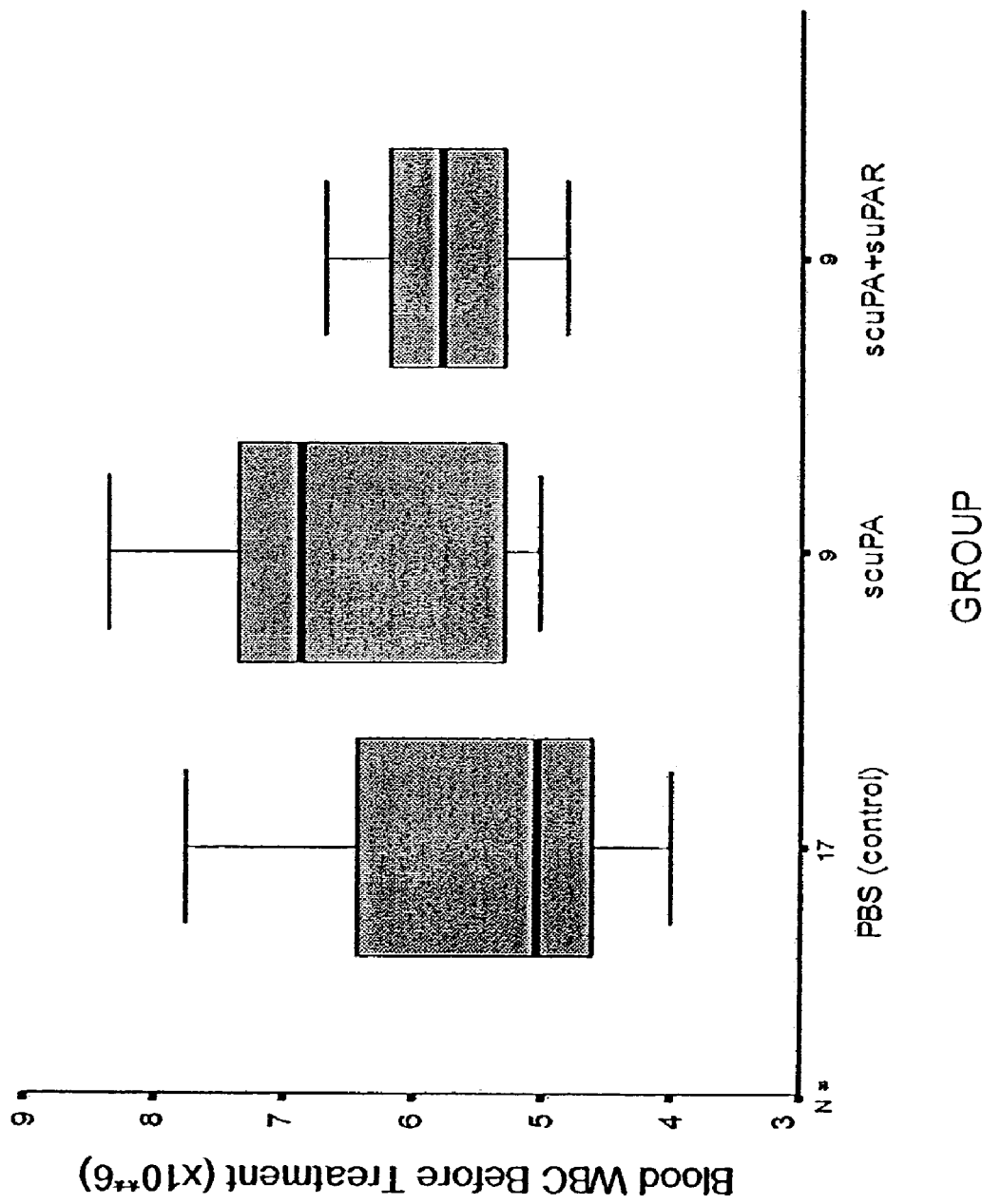
FIG. 12. Total White Blood Cell Counts in Peripheral Blood of Rabbits Before Treatment with scuPA, scuPA-suPAR or PBS.
Figure 13:
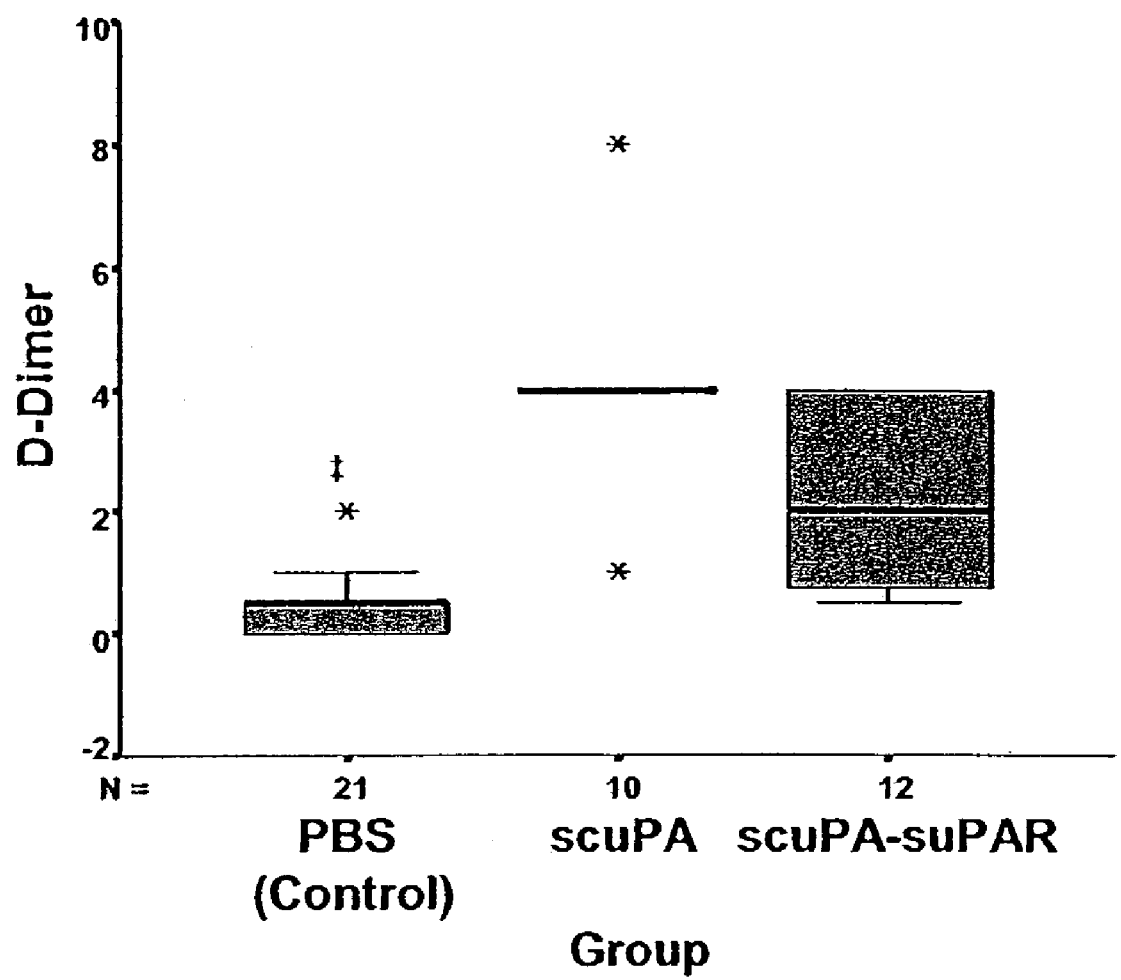
FIG. 13. D-Dimer concentrations in pleural fluids of scuPA, scuPA-suPAR and PBS vehicle treated rabbits with TCN-induced pleural injury. (‡) PBS group lower than other groups, p<0.001.
Figure 14:
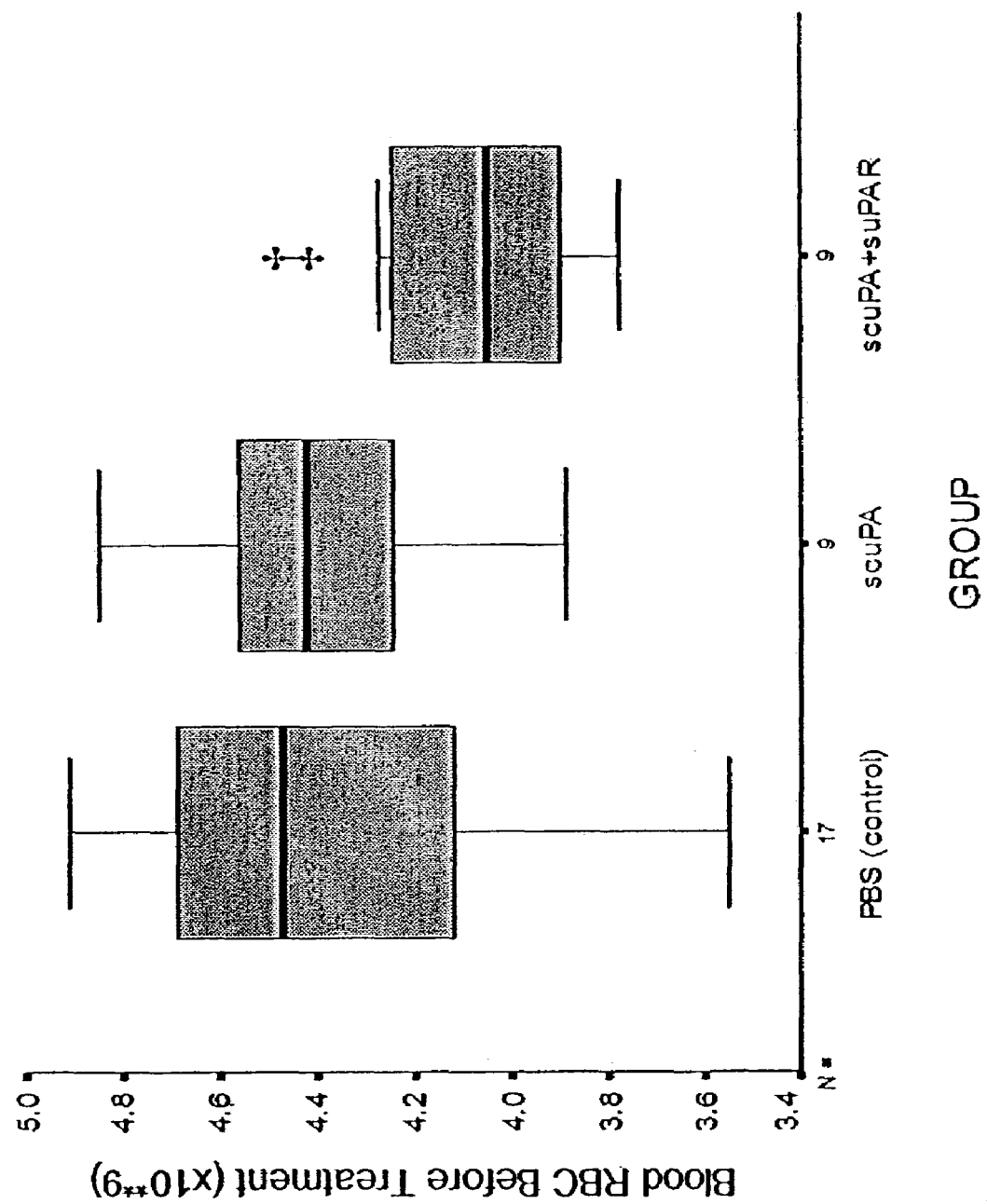
FIG. 14. Total Red Blood Cell Counts in Peripheral Blood of Rabbits Before Treatment with scuPA, scuPA-suPAR or PBS. (‡) scuPA-suPAR group lowest, p=0.04.
Figure 15:
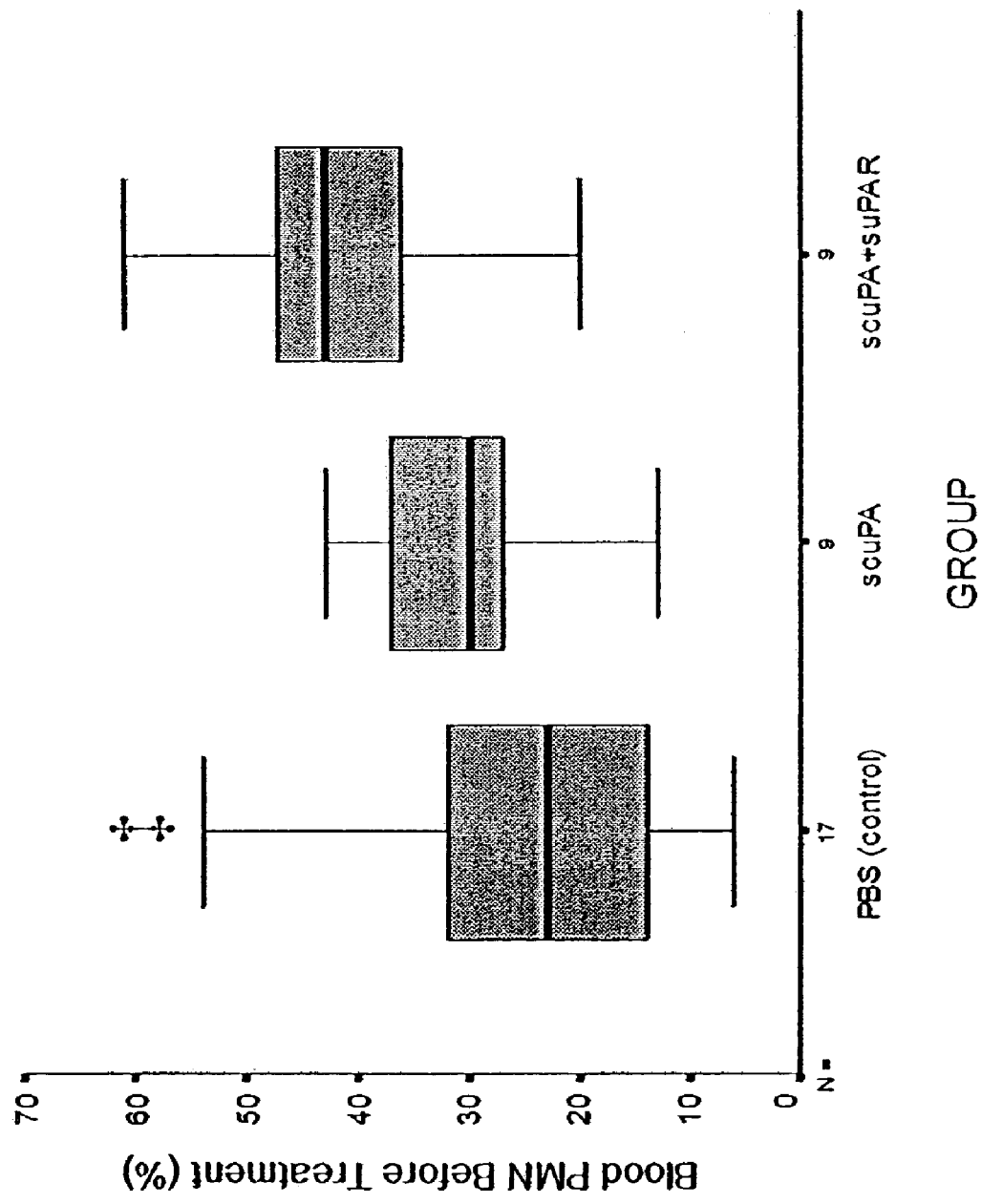
FIG. 15. Neutrophil Counts in Peripheral Blood of Rabbits Before Treatment with scuPA, scuPA-suPAR or PBS. (‡) PBS group is the lowest, p=0.006.
Figure 16:
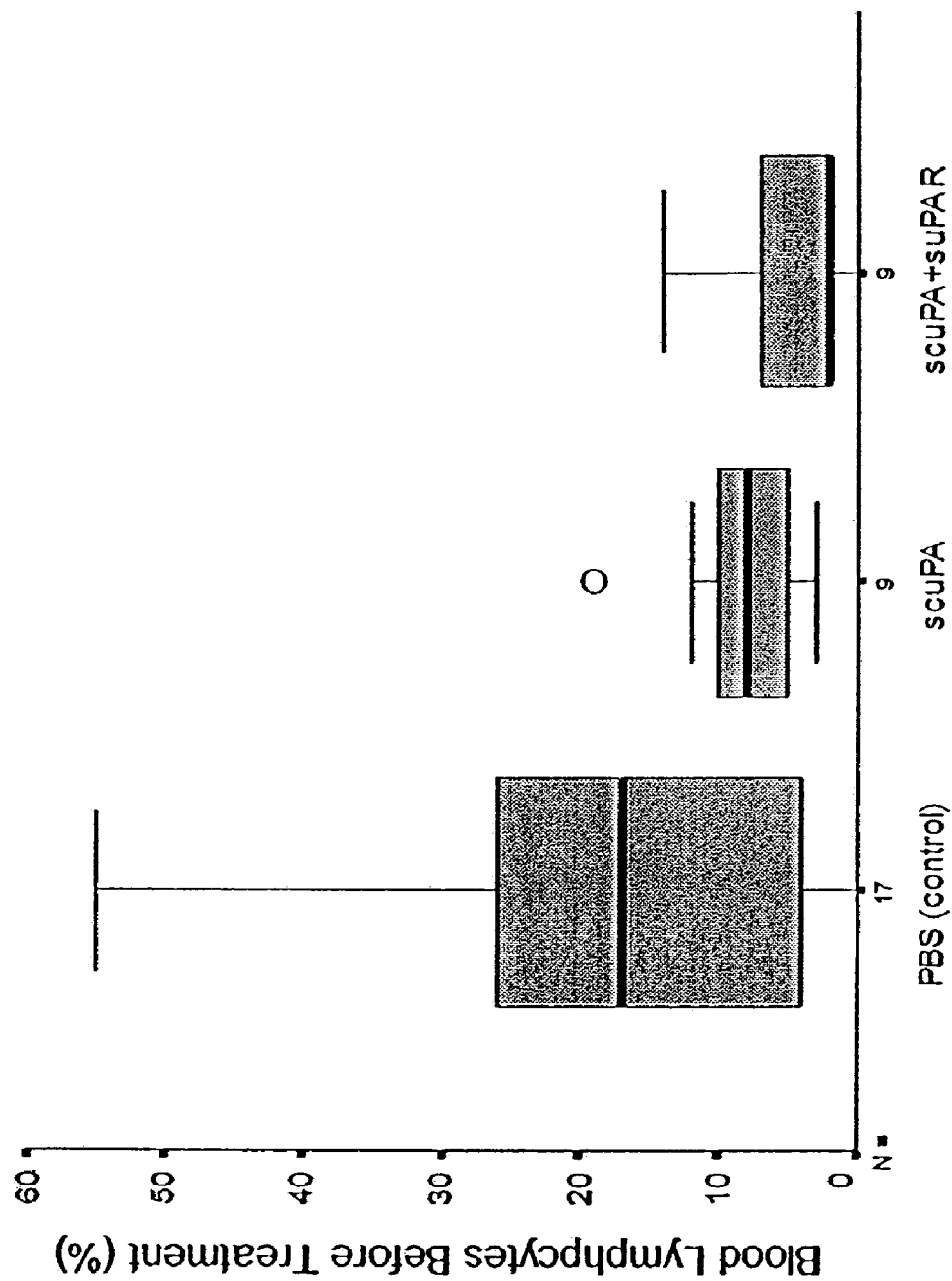
FIG. 16. Lymphocyte Counts in Peripheral Blood of Rabbits Before Treatment with scuPA, scuPA-suPAR or PBS.
Figure 17:
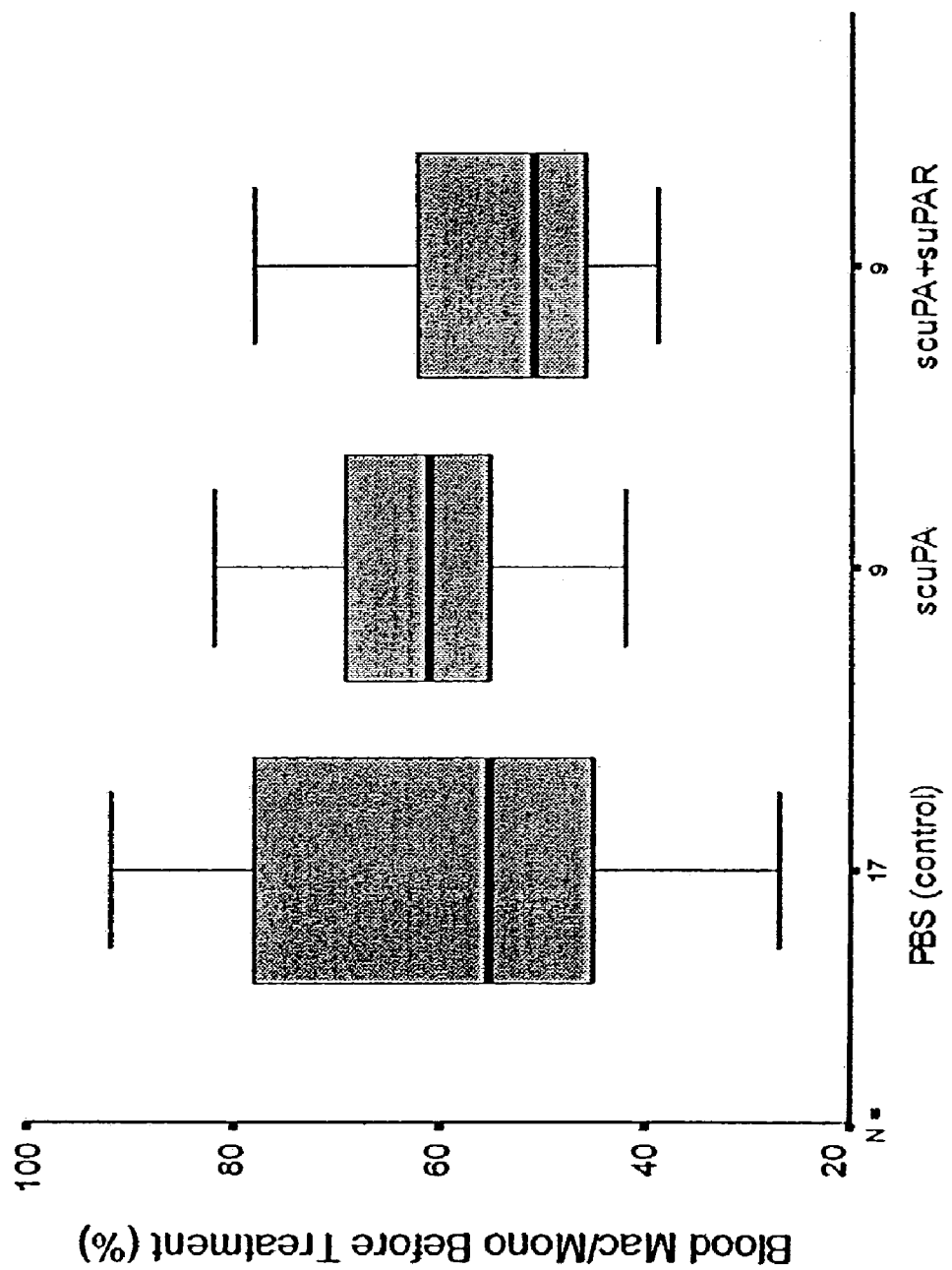
FIG. 17. Macrophages/Monocytes in Peripheral Blood of Rabbits Before Treatment with scuPA, scuPA-suPAR or PBS.
Figure 18:
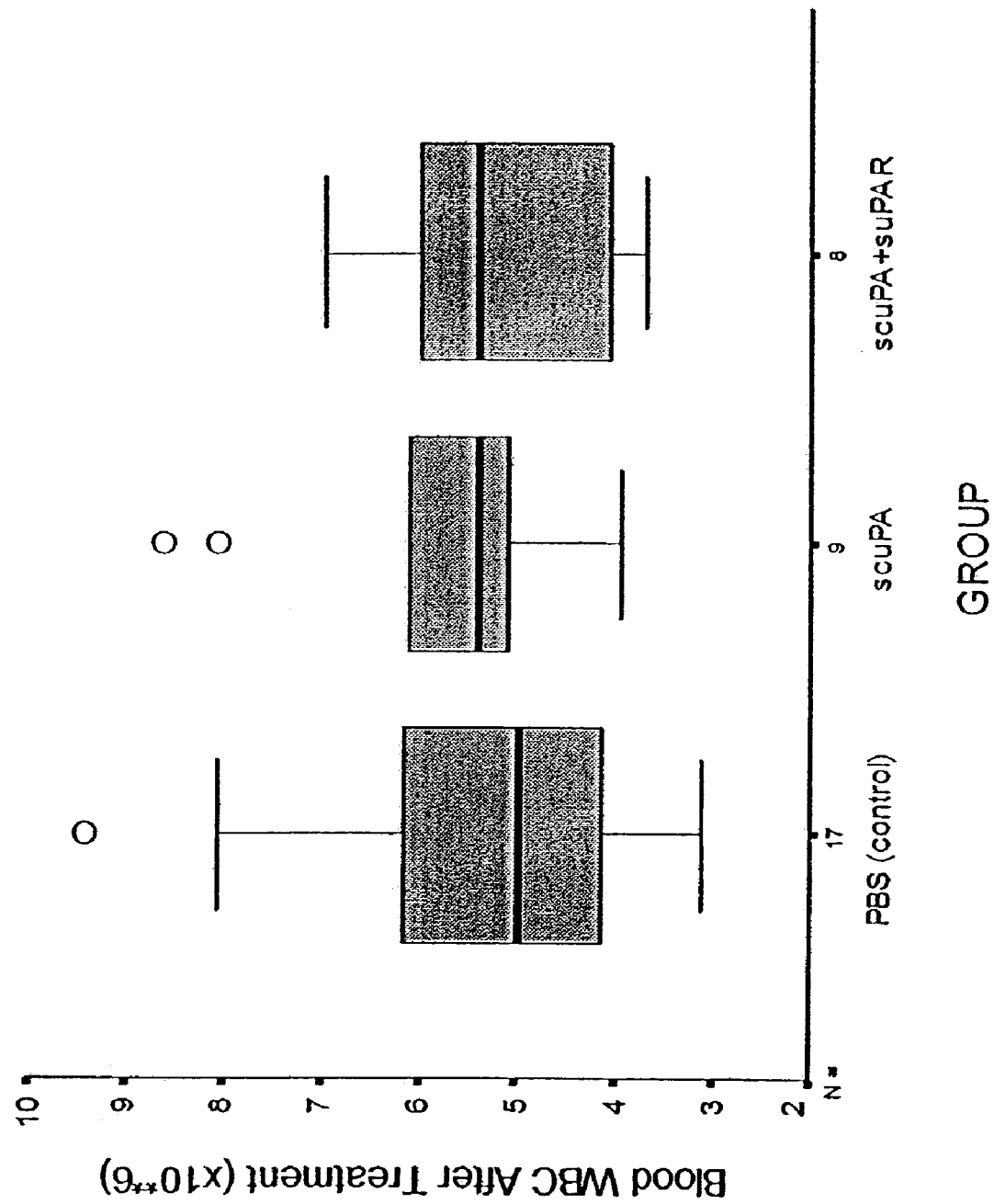
FIG. 18. Total White Cells in Peripheral Blood After Treatment with scuPA, scuPA-suPAR or PBS.
Figure 19:
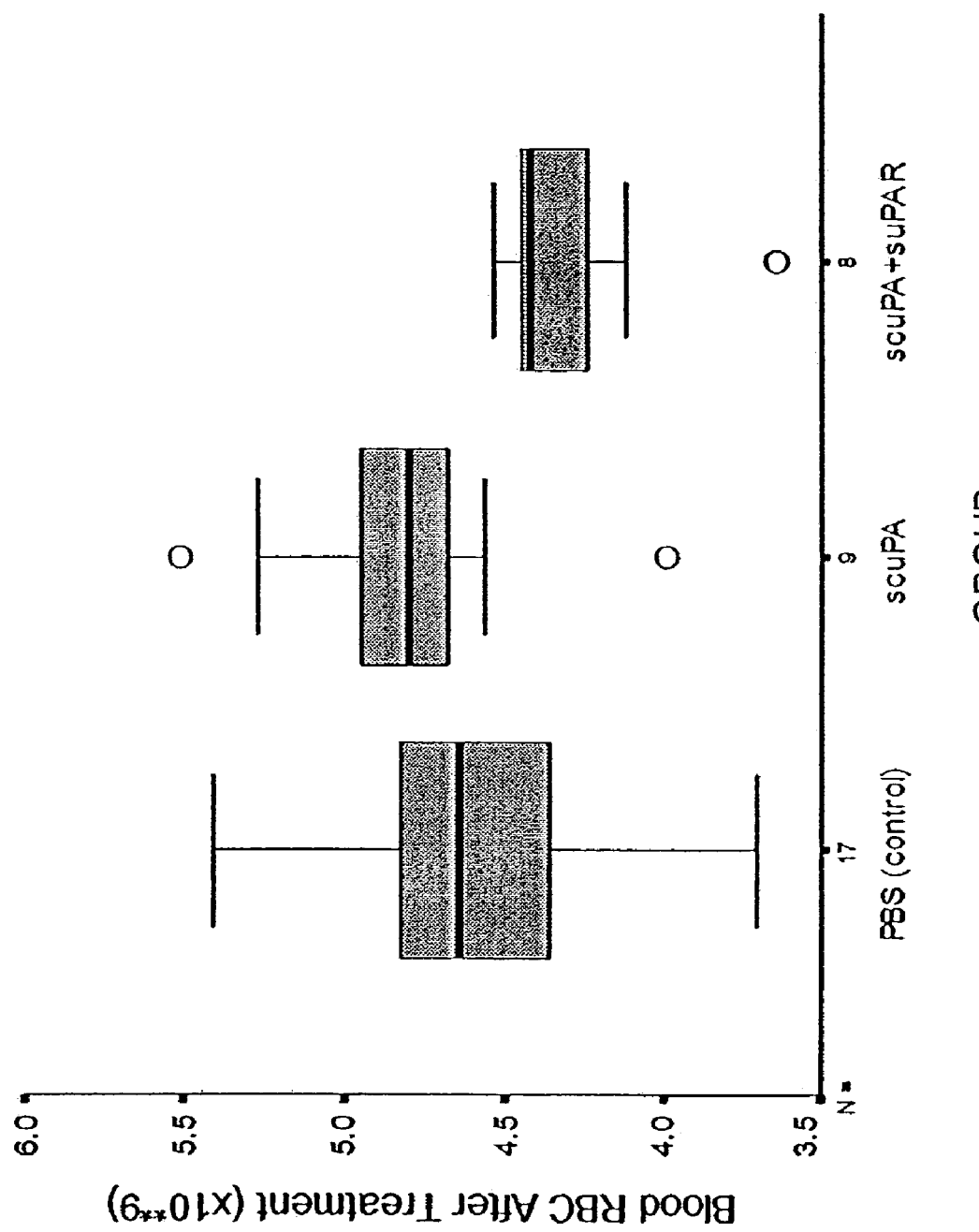
FIG. 19. Total Red Blood Cells in Peripheral Blood After Treatment with scuPA, scuPA-suPAR or PBS.
Figure 20:
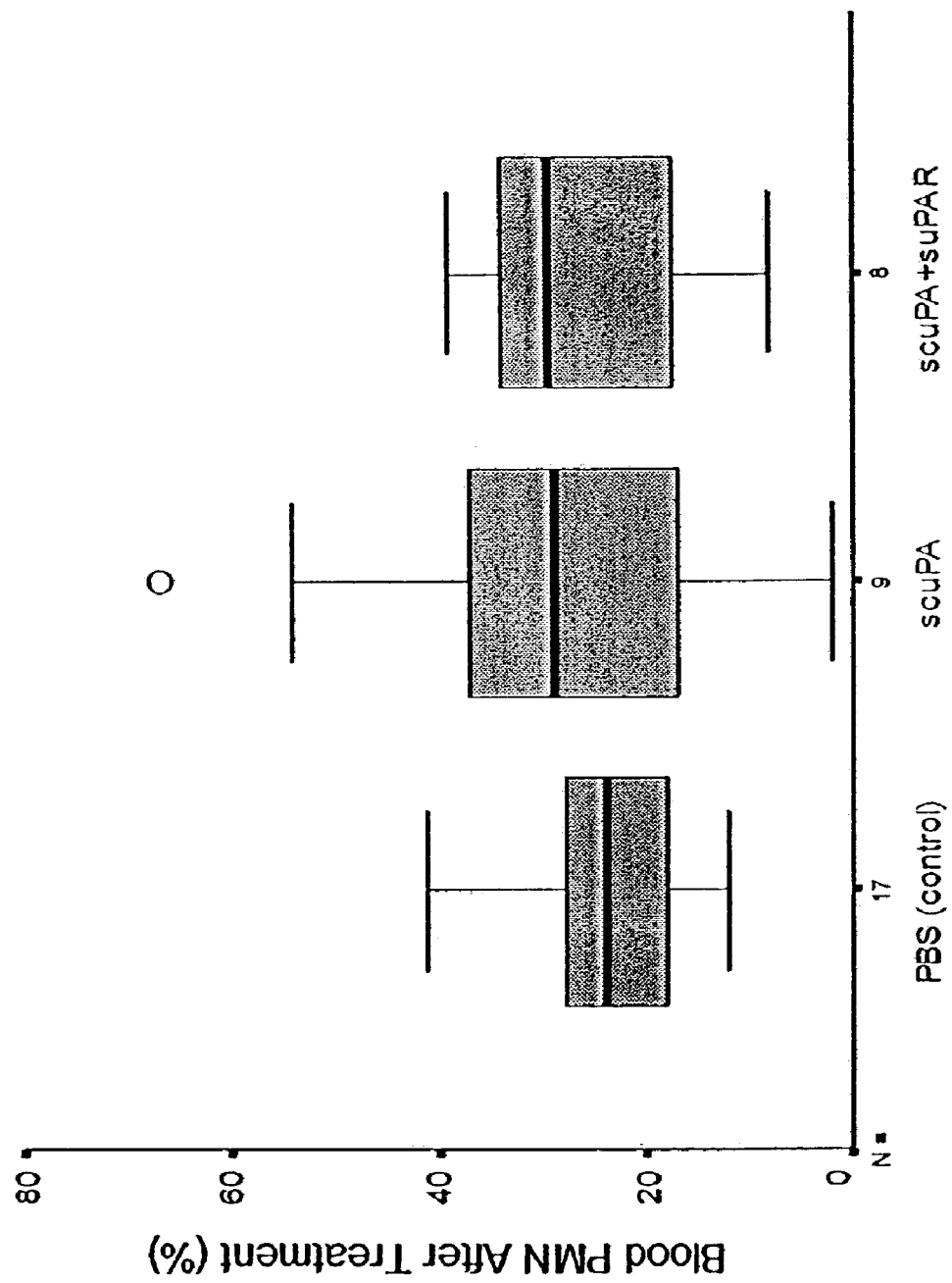
FIG. 20. Neutrophil Counts in Peripheral Blood After Treatment with scuPA, scuPA-suPAR or PBS.
Figure 21:
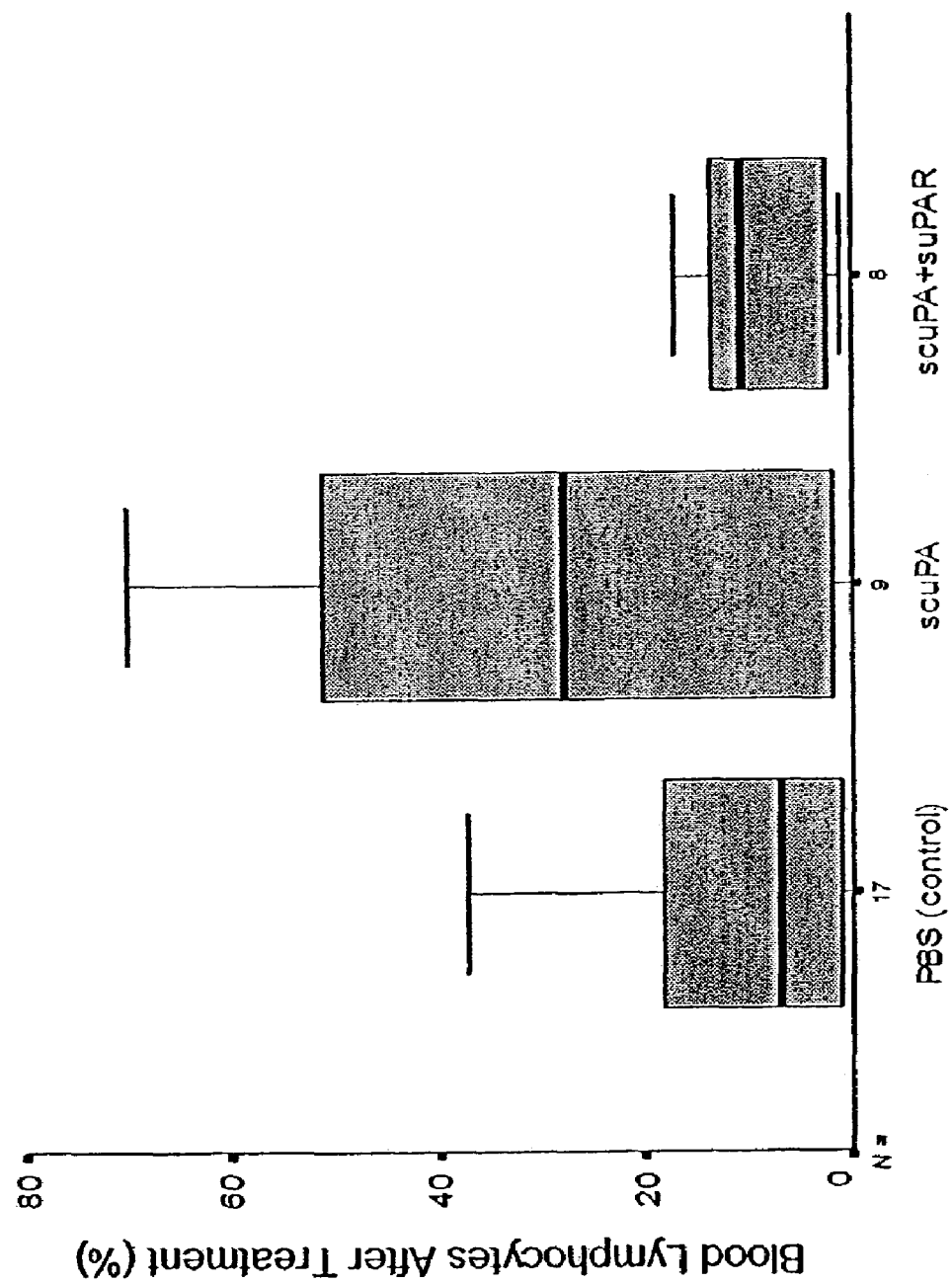
FIG. 21. Lymphocyte Counts in Peripheral Blood After Treatment with scuPA, scuPA-suPAR or PBS.
Figure 22:
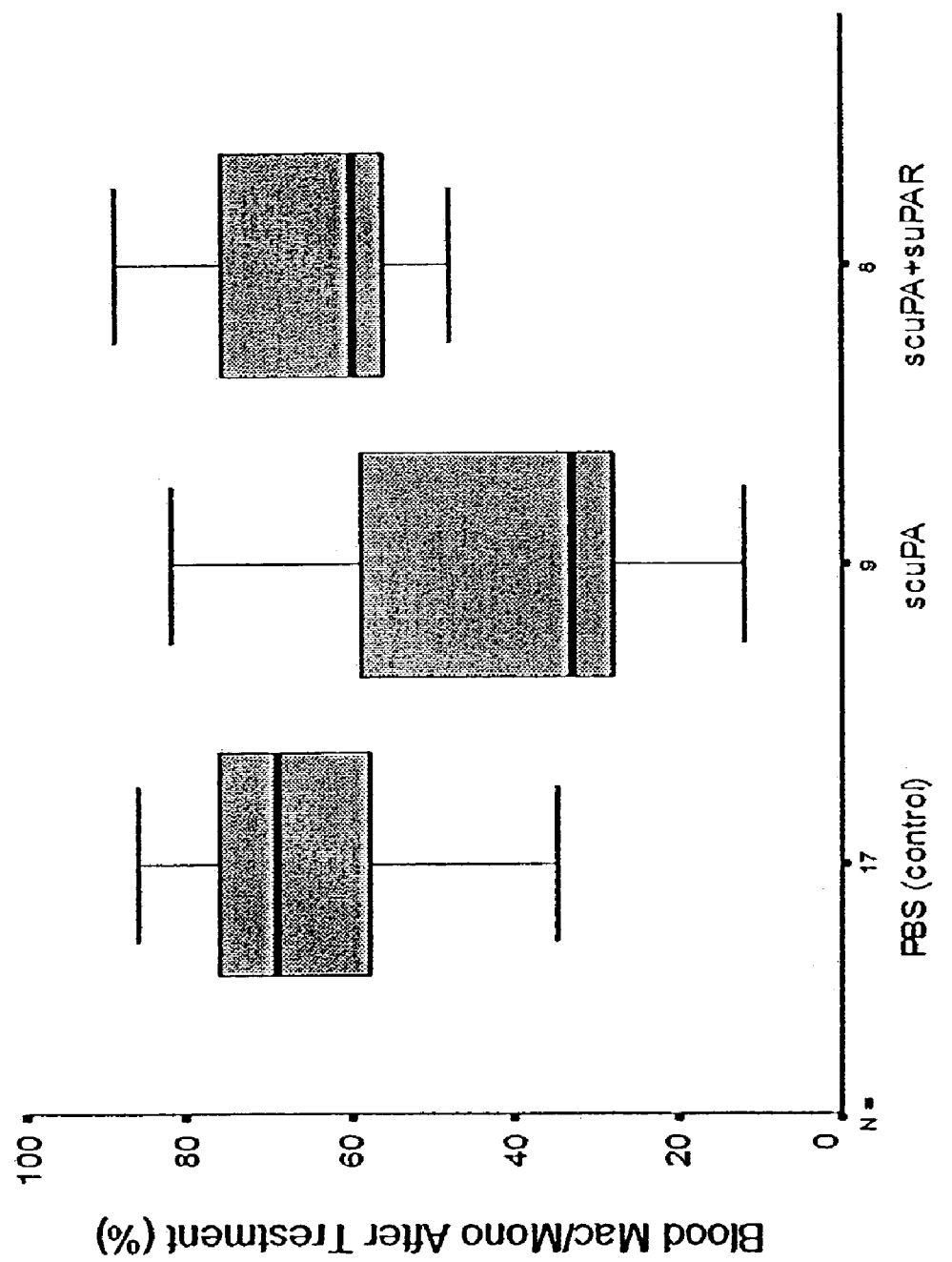
FIG. 22. Macrophages/monocytes in Peripheral Blood After Treatment with scuPA, scuPA-suPAR or PBS.
Figure 23:
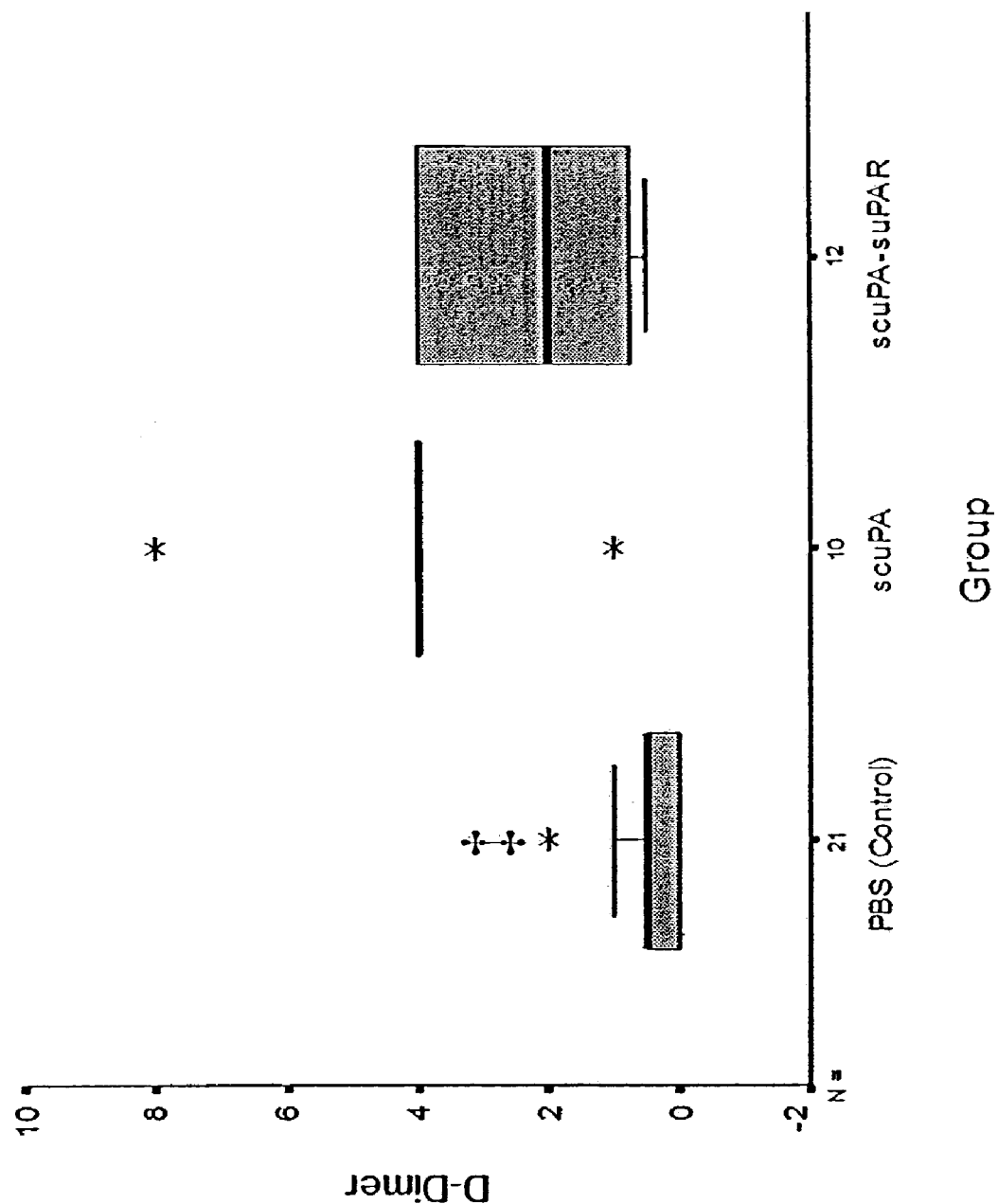
FIG. 23. D-Dimer in Pleural Fluids of Rabbits Treated with Intrapleural scuPA, scuPA-suPAR or PBS. (‡) PBS group lower than each of the other groups, p<0.001.
Figure 24:
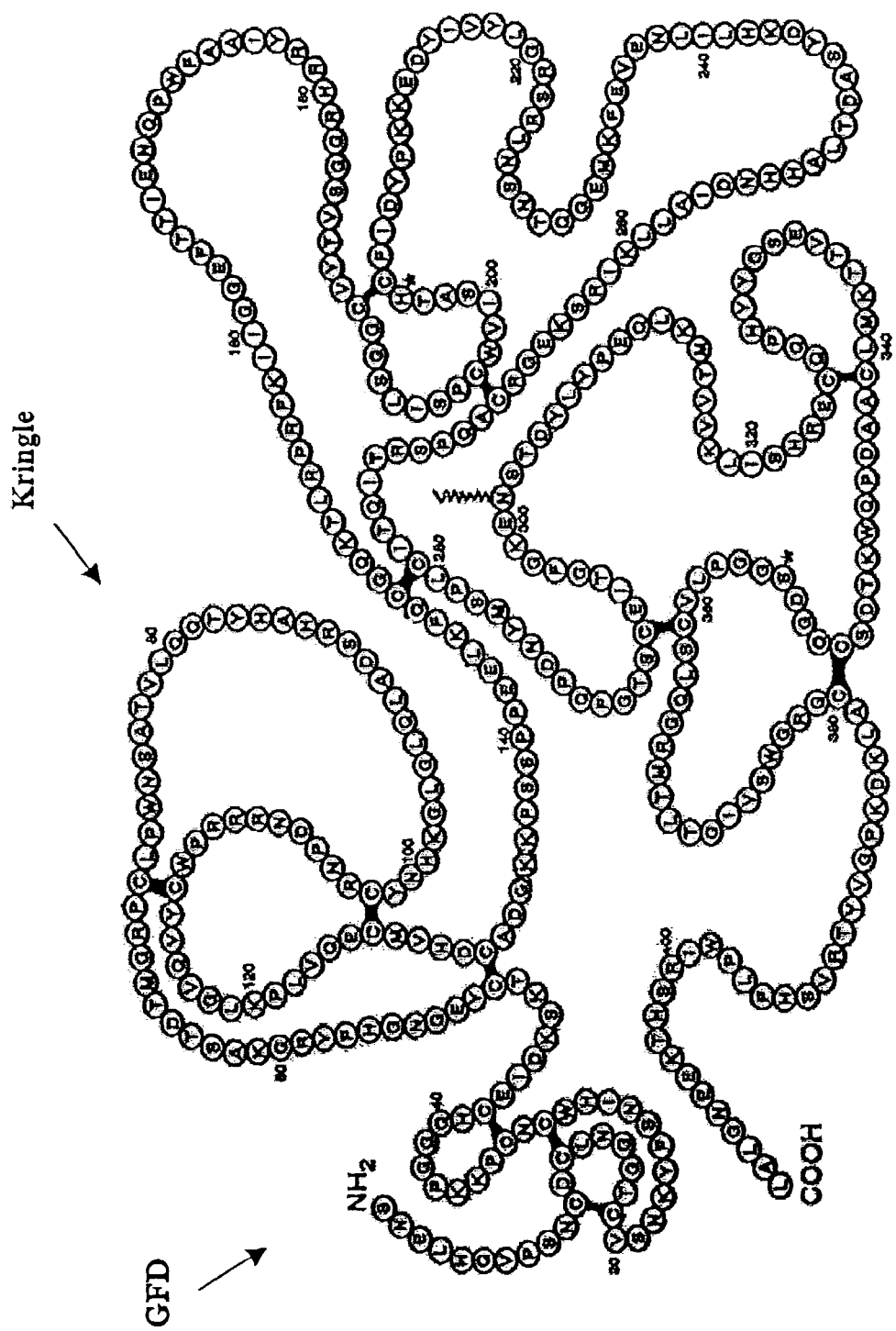
FIG. 24. Diagram of single chain plasminogen activator (scuPA), amino acid residues 1-411 of the mature human sequence.
Figure 25:
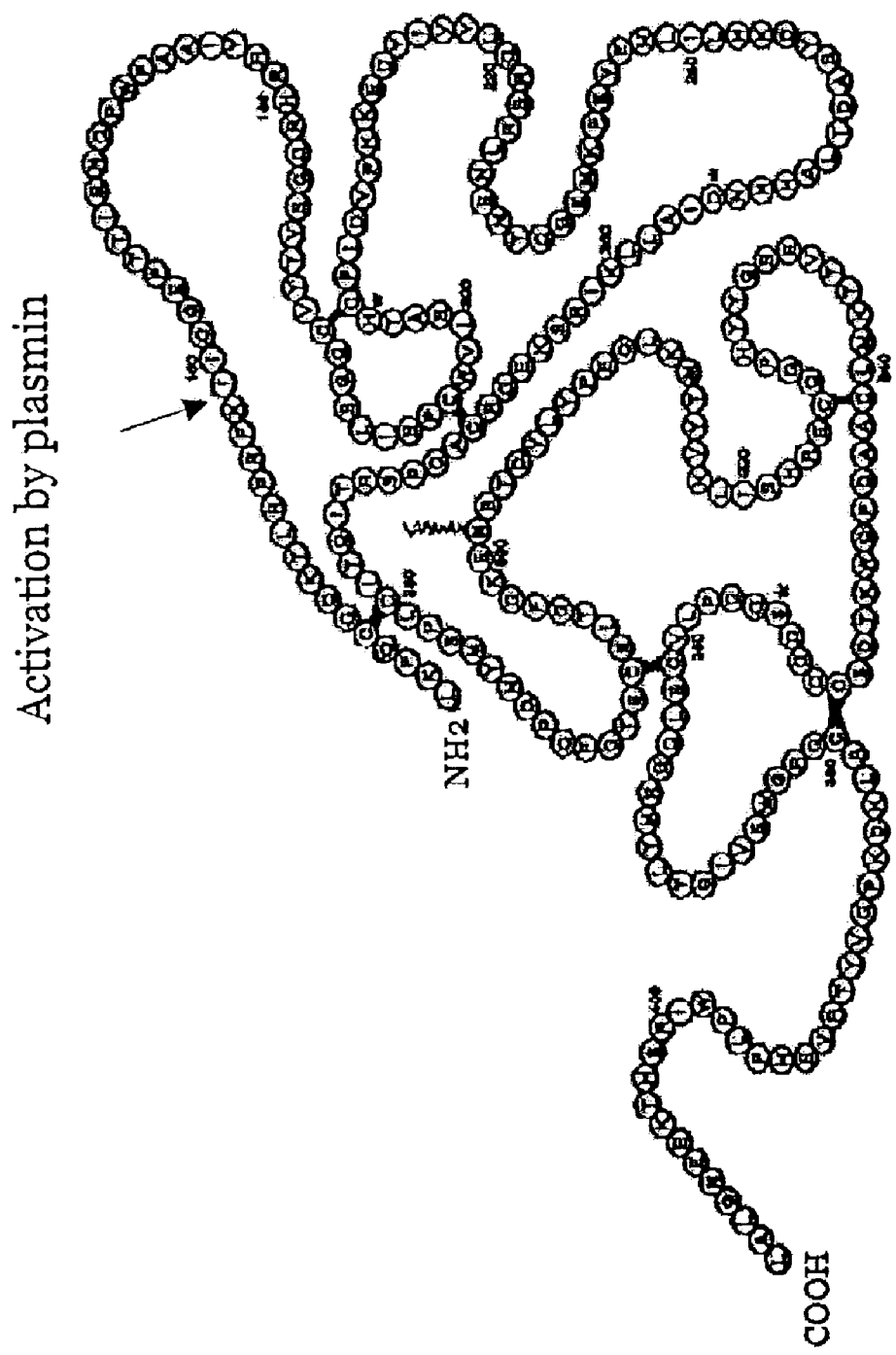
FIG. 25. Diagram of low molecular weight (LMW) plasminogen activator, amino acid residues 164-411 of the mature human sequence.

Pleural Fluid Recalcification Times and D-dimer Concentrations. The inventors have previously shown that the pleural fluids in this model contain several procoagulants, including tissue factor (Idell et al, 1998). The inventors therefore chose to analyze the aggregate procoagulant activity of the pleural fluids by measurement of the recalcification times, as the inventors previously reported in this model (Strange et al., 1995). There were no significant differences in pleural fluid recalcification times (p=0.15) (FIG. 11). The median recalcification time in the TCN-PBS pleural fluids was 290 sec (range 208-477 sec) versus 317 sec (207-549 sec) and 247 sec (170-294 sec) in the TCN-scuPA and TCN-scuPA-suPAR groups, respectively. The control recalcification time of sterile saline in pooled rabbit plasma was 464 sec, indicating that comparable levels of pleural fluid procoagulant activity was generally detectable in pleural fluids from all three groups. D-dimer concentrations were significantly increased in pleural fluids of scuPA or scuPA-suPAR-treated rabbits versus those of rabbits treated with intrapleural vehicle (FIGS. 12 and 13), indicating that local fibrinolytic activity was increased in the pleural fluids of rabbits treated with either interventional agent.

Example 9

Peripheral Blood Cell Counts Before and After Pleural Injury. Blood cell counts before pleural injury are represented in FIG. 14-FIG. 18 and after pleural injury are represented in FIG. 19-FIG. 23. When all groups were compared, the peripheral blood red cell (RBC) counts measured before induction of pleural injury were significantly lower in the TCN scuPA-suPAR group (median: $4.13 \times 10^9$, range: $3.87-4.27 \times 10^9$ cells) versus that of the TCN-PBS (median: $4.47 \times 10^9$, $3.55-4.91 \times 10^9$ cells) or TCN-scuPA— treated animals (median: $4.42 \times 10^9$, $3.89$-$4.85 \times 10^9$ cells). After injury, the peripheral blood RBC count rose at 72 h when compared to baseline levels (p<0.0001, all groups were considered). In the TCN-PBS group, the RBC counts after injury rose to a median level of $4.64 \times 10^9$ cells, p=0.004 versus baseline). In the TCN-scuPA group, the RBC counts rose to a median of $4.80 \times 10^9$ cells, p=0.008, while the same trend was observed in the TCN-scuPA-suPAR group: median: $4.42 \times 10^9$ cells, p=0.09. There was an increase in the peripheral RBC counts after injury in all but 4 animal; in 3 TCN-PBS and 1 TCN scuPA-suPAR-treated animal, there were mild (<10%) decreases noted after injury. These data indicate that the neither of the intrapleural fibrinolysins caused detectable systemic blood loss or acute anemia.

There was no significant difference between the peripheral WBC counts (range of medians $5.04$-$6.87 \times 10^6$ cells/ml of the groups either before or after injury (p=0.06 and p=0.52, respectively). While the percentage of PMN on differential WBC counts in the TCN-PBS group (median 23, range 6-54%) was significantly lower before injury versus the TCN-scuPA (30, 13-43%) and TCN-scuPA-suPAR groups (44, 20-61%), there was no difference in the % PMNs after injury in any of the groups (p=0.69). There was no significant difference in the change of the % PMN compared to the baseline before injury in the TCN-PBS or TCN-scuPA groups (p=0.85 and 0.95, respectively), while that in the TCN-scuPA-suPAR group fell to 29% after injury (p=0.02). There were no significant differences in the change of the percentage of lymphocytes and monocytes in peripheral blood before and after injury in the TCN-PBS and TCN-scuPA groups. In the TCN-scuPA-suPAR group, the percentage of lymphocytes rose from a baseline of 2% to 10.5% after injury (p=0.02).

Example 10

Preclincal and Clinical Trials of scuPA and/or scuPA mimetics. In order to conduct preclinical and clinical trials, one of ordinary skill will employ standard methodologies that are known in the art, inlcuding, in some cases, the dosage, formulation, treatment regimes, and analysis methodologies discussed herein and variations thereof. A scuPA or scuPA mimetic can be administered to a subject either intrapleurally, directly, by aerosol or any method disclosed herein. The presence of the level of uPA related antigen in the fluids of the treated subject after administration is measured and the decrease or prevention of scarring, injury or adhesion formation is noted.

REFERENCES

The following references, to the extent that they provide exemplary procedural or other details supplementary to those set forth herein, are specifically incorporated herein by reference.

U.S. Pat. No. 4,554,101
U.S. Pat. No. 5,548,158
U.S. Pat. No. 5,641,515
U.S. Pat. No. 5,399,363
U.S. Pat. No. 5,846,233
U.S. Pat. No. 5,846,225
U.S. Pat. No. 5,466,468
Antony et al., *Am. J. Respir. Cell Mol. Biol.*, 12:581-588. 1995.
Appella et al., *J. Biol. Chem.*, 262(10):4437-4440, 1987.
Baipai and Baker, *Biochem. Biophys. Res. Commun.*, 133 (2):475-482, 1985.
Boyd et al, *Cancer Research*, 48:3112-3116, 1988.
Brott and Bogousslavsky, *N. Engl. J. Med.*, 343[10], 710-722. 2000.
Cameron, *Cochrane Database Syst. Rev.*, 3:002312, 2000.
Colice et al., *Chest*, 18:1158-1171, 2000.
Coleman and Benach, *J. Lab. Clin. Med.*, 134:567, 1999.
Cubeilis et al, *J. Biol. Chem.*, 261(34):15819-15822, 1986.
Davies et al., *Am. J. Respir. Crit. Care Med.*, 157:328-330, 1998.
de Souza et al., *Am. J. Surg.*, 180:507-511, 2000.
Dvorak, NE *J. Med.*, 315:1650-1659, 1986.
Eaton et al., *J. Biol. Chem.*, 259(10):6241-6247, 1984.
Handley et al., *J. Virol.*, 70:4451, 1996.
Higazi et al., *Blood*, 87:3545-3549, 1996.
Higazi et al., *Blood*, 92:2075-2083. 1998.
Higazi, *J. Biol. Chem.*, 270:17375-17380,1995.
Idell et al., *Amer. Rev. Respir. Dis.*, 144:187-194, 1991.
Idell et al., *Thromb. and Haemost.*, 79:649-655, 1998.
Idell, In: *Pulmonary Fibrosis*, Thrall and Phan (Eds.), NY, Marcel Dekker, 80:743-776. 1995.
Idell, *New Horizons*, 2:566-574, 1994.
Johnson et al., In: *Biotechnology And Pharmacy*, Pezzuto et al., Chapman and Hall (Eds.), NY, 1993.
Kasai et al., *J. Biol. Chem.*, 260:12382, 1985.
Kyte and Doolittle, *J. Mol. Biol.*, 157(1):105-32, 1982.
Light et al., *Clin. Chest Med.*, 19:373-382, 1998.
Light, "Hemothorax," In: *Pleural Diseases*, 4th ed. Lippincott williams and Wilkins, Philadelphia, 151-181 and 320-326, 2001.
Manchanda, *J. Biol. Chem.*, 270:20032-20035, 1995.
Mazar et al., *Angiogenesis*, 3:15-32. 1999.
Miller et al., *Europ. Respir. J.*, 14: 1387-1393, 1999.
Needham et al., *Br. J. Cancer*, 55:13-16, 1987.
Nielsen et al., *J. Biol. Chem.*, 263:2358, 1988.
Pannell and Gurewich, *Blood*, 69:22, 1987.
Perkins et al., *Amer. J. Respir. Cell Molec. Biol.*, 21:637-646, 1999.
Ploug et al., *J. Biol. Chem.*, 273:13933, 1998.
Plow et al., *J. Cell Biol.*, 103(6):2411-2420, 1986.
Sahn, *Am. Rev. Respir. Dis.*, 138:184-234, 1988.
Sahn, In: *Pleural Disease*, 2ed. American College of Physicians and Amer. Soc. Internal Med., 262-283, 1998.
Sahn, *Thorax*, 53(2):S65-S72, 1998.
Sambrook et al., In: *Molecular cloning*, Cold Spring Harbor Laboratory Press, Cold Spring Harbor, N.Y., 2001.
Shetty and Idell, *Amer. J. Physiol.*, 274:L871-L882, 1998.
Shetty et al., *Amer. J. Respir. Cell Molec. Biol.*, 15:78-87, 1996.
Skriver et al., *J. Cell Biol.*, 99:752-757, 1984.
Stoppelli et al., *Proc. Natl. Acad. Sci. USA*, 82:4939, 1985.
Strange et al., *Amer. J. Respir. Critical Care Med.*, 151:508-515, 1995.
Tarui et al., *J. Biol. Chem.*, 276(6):3983-3990. 2001.
Tillett and Sherry, *J. Clin. Invest.*, 28:173-190, 1949.
Vassalli et al., *J. Cell. Biol.*, 100:86, 1985.

What is claimed is:

1. A method of decreasing the severity of pleural scarring in a subject after an injury that occurs as a result of pneumonia, chemical, irradiation or hyperoxic lung injury, particulate lung injury, or interstitial lung disease, which method comprises:

intrapleurally administering to a subject in need thereof an effective amount of a pharmaceutical composition comprising single chain urokinase plasminogen activator (scuPA) polypeptide that is characterized by the presence of an N-terminal growth factor domain and a kringle region and a C-terminal serine protease domain, thereby decreasing pleural scarring in the subject relative to an amount of pleural scarring that would be expected if the pharmaceutical composition were not administered.

2. The method of claim 1, wherein the scuPA polypeptide is bound to a scuPA receptor prior to administration.

3. The method of claim 1, wherein the scuPA is recombinant human scuPA.

4. The method of claim 1, wherein the amino acid sequence of the scuPA is SEQ ID NO:2.

5. A method of decreasing the severity of pleural scarring in a subject that occurs as a result of pneumonia, chemical, irradiation or hyperoxic lung injury, particulate lung injury, or interstitial lung disease, comprising intrapleurally administering to a subject in need thereof an effective amount of a pharmaceutical composition comprising a low molecular weight single chain urokinase plasminogen activator (scuPA) polypeptide, which is the scuPA polypeptide from which an N-terminal growth factor domain and kringle region have been deleted, but which maintains a C-terminal serine protease domain, thereby decreasing the pleural scarring relative to an amount of pleural scarring that would be expected if the pharmaceutical composition were not administered.

6. The method of claim 5, wherein the amino acid sequence of the low molecular weight scuPA is SEQ ID NO:3.

* * * * *

SEQUENCE LISTING

<160> NUMBER OF SEQ ID NOS: 3

<210> SEQ ID NO 1
<211> LENGTH: 1236
<212> TYPE: DNA
<213> ORGANISM: Homo sapiens
<220> FEATURE:
<221> NAME/KEY: CDS
<222> LOCATION: (1)..(1236)

<400> SEQUENCE: 1

| | | | | | | | | | | | | | | | | |
|---|---|---|---|---|---|---|---|---|---|---|---|---|---|---|---|---|
| agc | aat | gaa | ctt | cat | caa | gtt | cca | tcg | aac | tgt | gac | tgt | cta | aat | gga | 48 |
| Ser | Asn | Glu | Leu | His | Gln | Val | Pro | Ser | Asn | Cys | Asp | Cys | Leu | Asn | Gly | |
| 1 | | | | 5 | | | | | 10 | | | | | 15 | | |
| gga | aca | tgt | gtg | tcc | aac | aag | tac | ttc | tcc | aac | att | cac | tgg | tgc | aac | 96 |
| Gly | Thr | Cys | Val | Ser | Asn | Lys | Tyr | Phe | Ser | Asn | Ile | His | Trp | Cys | Asn | |
| | | | 20 | | | | | 25 | | | | | 30 | | | |
| tgc | cca | aag | aaa | ttc | gga | ggg | cag | cac | tgt | gaa | ata | gat | aag | tca | aaa | 144 |
| Cys | Pro | Lys | Lys | Phe | Gly | Gly | Gln | His | Cys | Glu | Ile | Asp | Lys | Ser | Lys | |
| | | 35 | | | | | 40 | | | | | 45 | | | | |
| acc | tgc | tat | gag | ggg | aat | ggt | cac | ttt | tac | cga | gga | aag | gcc | agc | act | 192 |
| Thr | Cys | Tyr | Glu | Gly | Asn | Gly | His | Phe | Tyr | Arg | Gly | Lys | Ala | Ser | Thr | |
| 50 | | | | | 55 | | | | | 60 | | | | | | |
| gac | acc | atg | ggc | cgg | ccc | tgc | ctg | ccc | tgg | aac | tct | gcc | act | gtc | ctt | 240 |
| Asp | Thr | Met | Gly | Arg | Pro | Cys | Leu | Pro | Trp | Asn | Ser | Ala | Thr | Val | Leu | |
| 65 | | | | | 70 | | | | | 75 | | | | | 80 | |
| cag | caa | acg | tac | cat | gcc | cac | aga | tct | gat | gct | ctt | cag | ctg | ggc | ctg | 288 |
| Gln | Gln | Thr | Tyr | His | Ala | His | Arg | Ser | Asp | Ala | Leu | Gln | Leu | Gly | Leu | |
| | | | | 85 | | | | | 90 | | | | | 95 | | |
| ggg | aaa | cat | aat | tac | tgc | agg | aac | cca | gac | aac | cgg | agg | cga | ccc | tgg | 336 |
| Gly | Lys | His | Asn | Tyr | Cys | Arg | Asn | Pro | Asp | Asn | Arg | Arg | Arg | Pro | Trp | |
| | | | 100 | | | | | 105 | | | | | 110 | | | |
| tgc | tat | gtg | cag | gtg | ggc | cta | aag | ctg | ctt | gtc | caa | gag | tgc | atg | gtg | 384 |
| Cys | Tyr | Val | Gln | Val | Gly | Leu | Lys | Leu | Leu | Val | Gln | Glu | Cys | Met | Val | |
| | | 115 | | | | | 120 | | | | | 125 | | | | |
| cat | gac | tgc | gca | gat | gga | aaa | aag | ccc | tcc | tct | cct | cca | gaa | gaa | tta | 432 |
| His | Asp | Cys | Ala | Asp | Gly | Lys | Lys | Pro | Ser | Ser | Pro | Pro | Glu | Glu | Leu | |
| 130 | | | | | 135 | | | | | 140 | | | | | | |
| aaa | ttt | cag | tgt | ggc | caa | aag | act | ctg | agg | ccc | cgc | ttt | aag | att | att | 480 |
| Lys | Phe | Gln | Cys | Gly | Gln | Lys | Thr | Leu | Arg | Pro | Arg | Phe | Lys | Ile | Ile | |
| 145 | | | | | 150 | | | | | 155 | | | | | 160 | |
| ggg | gga | gaa | ttc | acc | acc | atc | gag | aac | cag | ccc | tgg | ttt | gcg | gcc | atc | 528 |
| Gly | Gly | Glu | Phe | Thr | Thr | Ile | Glu | Asn | Gln | Pro | Trp | Phe | Ala | Ala | Ile | |
| | | | | 165 | | | | | 170 | | | | | 175 | | |
| tac | agg | agg | cac | cgg | ggg | ggc | tct | gtc | acc | tac | gtg | tgt | gga | ggc | agc | 576 |
| Tyr | Arg | Arg | His | Arg | Gly | Gly | Ser | Val | Thr | Tyr | Val | Cys | Gly | Gly | Ser | |
| | | | 180 | | | | | 185 | | | | | 190 | | | |
| ctc | atc | agc | cct | tgc | tgg | gtg | atc | agc | gcc | aca | cac | tgc | ttc | att | gat | 624 |
| Leu | Ile | Ser | Pro | Cys | Trp | Val | Ile | Ser | Ala | Thr | His | Cys | Phe | Ile | Asp | |
| | | 195 | | | | | 200 | | | | | 205 | | | | |
| tac | cca | aag | aag | gag | gac | tac | atc | gtc | tac | ctg | ggt | cgc | tca | agg | ctt | 672 |
| Tyr | Pro | Lys | Lys | Glu | Asp | Tyr | Ile | Val | Tyr | Leu | Gly | Arg | Ser | Arg | Leu | |
| | 210 | | | | | 215 | | | | | 220 | | | | | |
| aac | tcc | aac | acg | caa | ggg | gag | atg | aag | ttt | gag | gtg | gaa | aac | ctc | atc | 720 |
| Asn | Ser | Asn | Thr | Gln | Gly | Glu | Met | Lys | Phe | Glu | Val | Glu | Asn | Leu | Ile | |
| 225 | | | | | 230 | | | | | 235 | | | | | 240 | |
| cta | cac | aag | gac | tac | agc | gct | gac | acg | ctt | gct | cac | cac | aac | gac | att | 768 |
| Leu | His | Lys | Asp | Tyr | Ser | Ala | Asp | Thr | Leu | Ala | His | His | Asn | Asp | Ile | |
| | | | | 245 | | | | | 250 | | | | | 255 | | |

```
gcc ttg ctg aag atc cgt tcc aag gag ggc agg tgt gcg cag cca tcc    816
Ala Leu Leu Lys Ile Arg Ser Lys Glu Gly Arg Cys Ala Gln Pro Ser
        260                 265                 270 cgg act ata cag acc atc tgc ctg ccc tcg atg tat aac gat ccc cag    864
Arg Thr Ile Gln Thr Ile Cys Leu Pro Ser Met Tyr Asn Asp Pro Gln
275                 280                 285 ttt ggc aca agc tgt gag atc act ggc ttt gga aaa gag aat tct acc    912
Phe Gly Thr Ser Cys Glu Ile Thr Gly Phe Gly Lys Glu Asn Ser Thr
        290                 295                 300 gac tat ctc tat ccg gag cag ctg aaa atg act gtt gtg aag ctg att    960
Asp Tyr Leu Tyr Pro Glu Gln Leu Lys Met Thr Val Val Lys Leu Ile
305                 310                 315                 320 tcc cac cgg gag tgt cag cag ccc cac tac tac ggc tct gaa gtc acc   1008
Ser His Arg Glu Cys Gln Gln Pro His Tyr Tyr Gly Ser Glu Val Thr
        325                 330                 335 acc aaa atg ctg tgt gct gct gac cca cag tgg aaa aca gat tcc tgc   1056
Thr Lys Met Leu Cys Ala Ala Asp Pro Gln Trp Lys Thr Asp Ser Cys
        340                 345                 350 cag gga gac tca ggg gga ccc ctc gtc tgt tcc ctc caa ggc cgc atg   1104
Gln Gly Asp Ser Gly Gly Pro Leu Val Cys Ser Leu Gln Gly Arg Met
        355                 360                 365 act ttg act gga att gtg agc tgg ggc cgt gga tgt gcc ctg aag gac   1152
Thr Leu Thr Gly Ile Val Ser Trp Gly Arg Gly Cys Ala Leu Lys Asp
370                 375                 380 aag cca ggc gtc tac acg aga gtc tca cac ttc tta ccc tgg atc cgc   1200
Lys Pro Gly Val Tyr Thr Arg Val Ser His Phe Leu Pro Trp Ile Arg
385                 390                 395                 400 agt cac acc aag gaa gag aat ggc ctg gcc ctc tga                   1236
Ser His Thr Lys Glu Glu Asn Gly Leu Ala Leu
                405                 410

<210> SEQ ID NO 2
<211> LENGTH: 411
<212> TYPE: PRT
<213> ORGANISM: Homo sapiens

<400> SEQUENCE: 2

Ser Asn Glu Leu His Gln Val Pro Ser Asn Cys Asp Cys Leu Asn Gly
 1               5                  10                  15

Gly Thr Cys Val Ser Asn Lys Tyr Phe Ser Asn Ile His Trp Cys Asn
                20                  25                  30

Cys Pro Lys Lys Phe Gly Gly Gln His Cys Glu Ile Asp Lys Ser Lys
            35                  40                  45

Thr Cys Tyr Glu Gly Asn Gly His Phe Tyr Arg Gly Lys Ala Ser Thr
        50                  55                  60

Asp Thr Met Gly Arg Pro Cys Leu Pro Trp Asn Ser Ala Thr Val Leu
65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Leu Leu Val Gln Glu Cys Met Val
        115                 120                 125

His Asp Cys Ala Asp Gly Lys Lys Pro Ser Ser Pro Glu Glu Leu
        130                 135                 140

Lys Phe Gln Cys Gly Gln Lys Thr Leu Arg Pro Arg Phe Lys Ile Ile
145                 150                 155                 160
```

```
Gly Gly Glu Phe Thr Thr Ile Glu Asn Gln Pro Trp Phe Ala Ala Ile
                165                 170                 175

Tyr Arg Arg His Arg Gly Gly Ser Val Thr Tyr Val Cys Gly Gly Ser
            180                 185                 190

Leu Ile Ser Pro Cys Trp Val Ile Ser Ala Thr His Cys Phe Ile Asp
        195                 200                 205

Tyr Pro Lys Lys Glu Asp Tyr Ile Val Tyr Leu Gly Arg Ser Arg Leu
210                 215                 220

Asn Ser Asn Thr Gln Gly Glu Met Lys Phe Glu Val Glu Asn Leu Ile
225                 230                 235                 240

Leu His Lys Asp Tyr Ser Ala Asp Thr Leu Ala His His Asn Asp Ile
            245                 250                 255

Ala Leu Leu Lys Ile Arg Ser Lys Glu Gly Arg Cys Ala Gln Pro Ser
        260                 265                 270

Arg Thr Ile Gln Thr Ile Cys Leu Pro Ser Met Tyr Asn Asp Pro Gln
    275                 280                 285

Phe Gly Thr Ser Cys Glu Ile Thr Gly Phe Gly Lys Glu Asn Ser Thr
290                 295                 300

Asp Tyr Leu Tyr Pro Glu Gln Leu Lys Met Thr Val Val Lys Leu Ile
305                 310                 315                 320

Ser His Arg Glu Cys Gln Gln Pro His Tyr Tyr Gly Ser Glu Val Thr
            325                 330                 335

Thr Lys Met Leu Cys Ala Ala Asp Pro Gln Trp Lys Thr Asp Ser Cys
        340                 345                 350

Gln Gly Asp Ser Gly Gly Pro Leu Val Cys Ser Leu Gln Gly Arg Met
    355                 360                 365

Thr Leu Thr Gly Ile Val Ser Trp Gly Arg Gly Cys Ala Leu Lys Asp
370                 375                 380

Lys Pro Gly Val Tyr Thr Arg Val Ser His Phe Leu Pro Trp Ile Arg
385                 390                 395                 400

Ser His Thr Lys Glu Glu Asn Gly Leu Ala Leu
            405                 410

<210> SEQ ID NO 3
<211> LENGTH: 268
<212> TYPE: PRT
<213> ORGANISM: Homo sapiens

<400> SEQUENCE: 3

Leu Lys Phe Gln Cys Gly Gln Lys Thr Leu Arg Pro Arg Phe Lys Ile
1               5                   10                  15

Ile Gly Gly Glu Phe Thr Thr Ile Glu Asn Gln Pro Trp Phe Ala Ala
            20                  25                  30

Ile Tyr Arg Arg His Arg Gly Gly Ser Val Thr Tyr Val Cys Gly Gly
        35                  40                  45

Ser Leu Ile Ser Pro Cys Trp Val Ile Ser Ala Thr His Cys Phe Ile
    50                  55                  60

Asp Tyr Pro Lys Lys Glu Asp Tyr Ile Val Tyr Leu Gly Arg Ser Arg
65                  70                  75                  80

Leu Asn Ser Asn Thr Gln Gly Glu Met Lys Phe Glu Val Glu Asn Leu
                85                  90                  95

Ile Leu His Lys Asp Tyr Ser Ala Asp Thr Leu Ala His His Asn Asp
            100                 105                 110

Ile Ala Leu Leu Lys Ile Arg Ser Lys Glu Gly Arg Cys Ala Gln Pro
        115                 120                 125
```

-continued

```
Ser Arg Thr Ile Gln Thr Ile Cys Leu Pro Ser Met Tyr Asn Asp Pro
    130                 135                 140

Gln Phe Gly Thr Ser Cys Glu Ile Thr Gly Phe Gly Lys Glu Asn Ser
145                 150                 155                 160

Thr Asp Tyr Leu Tyr Pro Glu Gln Leu Lys Met Thr Val Val Lys Leu
                165                 170                 175

Ile Ser His Arg Glu Cys Gln Gln Pro His Tyr Tyr Gly Ser Glu Val
            180                 185                 190

Thr Thr Lys Met Leu Cys Ala Ala Asp Pro Gln Trp Lys Thr Asp Ser
        195                 200                 205

Cys Gln Gly Asp Ser Gly Gly Pro Leu Val Cys Ser Leu Gln Gly Arg
    210                 215                 220

Met Thr Leu Thr Gly Ile Val Ser Trp Gly Arg Gly Cys Ala Leu Lys
225                 230                 235                 240

Asp Lys Pro Gly Val Tyr Thr Arg Val Ser His Phe Leu Pro Trp Ile
                245                 250                 255

Arg Ser His Thr Lys Glu Glu Asn Gly Leu Ala Leu
            260                 265
```